(12) United States Patent
Eguchi et al.

(10) Patent No.: US 6,346,385 B1
(45) Date of Patent: Feb. 12, 2002

(54) ANALYSIS OF PREDISPOSITION BASED ON HUMAN AIRWAY TRYPSIN PROTEASE GENE POLYMORPHISM

(75) Inventors: Hiroshi Eguchi; Kazuyoshi Yamaoka; Kenichi Masuda, all of Tokyo; Susumu Yasuoka, Tokushima, all of (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/581,617

(22) PCT Filed: Dec. 16, 1998

(86) PCT No.: PCT/JP98/05689

§ 371 Date: Jun. 15, 2000

§ 102(e) Date: Jun. 15, 2000

(87) PCT Pub. No.: WO99/31271

PCT Pub. Date: Jun. 24, 1999

(30) Foreign Application Priority Data

Dec. 16, 1997 (JP) ............................... 9-346494

(51) Int. Cl.[7] ............................ C12Q 1/68; C12Q 1/44; C12P 19/34; C07H 21/04
(52) U.S. Cl. ............................ 435/6; 435/19; 435/91.2; 536/23.1; 536/23.2; 536/23.5; 536/24.31; 536/24.33
(58) Field of Search ............................ 435/6, 19, 91.2; 536/23.1, 23.2, 23.5, 24.31, 24.33

(56) References Cited

FOREIGN PATENT DOCUMENTS

| JP | 7-67640 | 3/1995 |
| JP | 8-89206 | 4/1996 |

OTHER PUBLICATIONS

J. Biol. Chem., vol. 273 [19] (1998), Yamaoka K. et al., "Cloning and Characterization of the cDNA for Human Airway Tripsin–like Protease" pp. 11895–11901 Copy submitted to USPTO by WIPO.

International Search Report, PCT/JP98/05689, Mar. 1999.

"Purification, Characterization, and Localization of a Novel Trypsin–like Protease Found in the Human Airway" by Yasuoka et al., Respir. Cell Mol. Biol., 16, 300–308, 1997.

"Cloning and Characterization of the cDNA for Human Airway Trypsin–like Protease" by Yamaoka et al., J. Biol. Chem. 273(19); 11895–11901, 1998.

Noriko Terao et al., the Japanese Respiratory Society, 1998, abstract.

Junko Yoshinaga et al., Conference on Proteases and Inhibitors in Pathophysiology and Therapeutics, 1998, abstract.

*Primary Examiner*—Carla J. Myers
*Assistant Examiner*—Diana Johannsen
(74) *Attorney, Agent, or Firm*—Sughrue Mion, PLLC

(57) ABSTRACT

A method for predicting the constitution susceptible to the onset of specific diseases in individual humans, for example, respiratory diseases such as chronic obstructive pulmonary diseases, sinobronchial syndrome, pulmonary emphysema, diffuse panbronchiolitis or bronchiectasis, effects of treatment on patients or prognosis of the treatment by analyzing the genetic polymorphisms of a human trypsin-like enzyme of the respiratory tract.

9 Claims, 9 Drawing Sheets

HpaI
      EcoRI       NlaIV              BsmI              BsII         NspHI    FokI          FokI
        ▼           ▼                 ▼                 ▼           ▼▼▼      ▼             ▼
    GAATTCGGCT TGGAGCCATC TTGTCTGGAA TGCTGTGTGC TGGAGTACCT CAAGGTGGAG TGGACGCATG TCAGGTAAGC TCAAGACAAT CTCATCCATG      100
    CTTAAGCCGA ACCTCGGTAG AACAGACCTT ACGACACACG ACCTCATGGA GTTCCACCTC ACCTGCGTAC AGTCCATTCG AGTCTGTTA GAGTAGGTAC
                                                                          ↑
                                                                    exon | intron C
                                                                         |
                                                                         |

TCATCATCCA AGAAGTGTAT AAGCACTTCC TAGTATGTGA TAATGTGATA GACATAAGTG TAACAGTTAC AATACACAGC CCTGTTCCTC TAAAATTTAT      200
    AGTAGTAGGT TCTTCACATA TTCGTGAAGG ATCATACACT ATTACACTAT CTGTATTCAC ATTGTCAATG TTATGTGTCG GGACAAGGAG ATTTTAAATA

HpaI
        XbaI                                     BspHI              HaeIII  FokI       HincII
         ▼                                         ▼                  ▼      ▼          ▼
    AATCTAGATT TTAGAAATAA ATTTTTTAT GAATGAAGTT TATCTATCAT GAAAGCATTA ACTCTGAGAG GCCAAATTAC AGAGTAGTTA ACCATCCAAA      300
    TTAGATCTAA AATCTTTATT TAAAAAAATA CTTACTTCAA ATAGATAGTA CTTTCGTAAT TGAGACTCTC CGGTTTAATG TCTCATCAAT TGGTAGGTTT TfiI         TaqI EcoRI
         ▼           ▼    ▼
    GCTCAAGAAT CAGAAAGACC TCGATTGAA TTCCTTAACC TCTATTACCA AGTCTCTTTA ACTAAAAGCT GGGGATAATC ATAATAGCAC CTAACTTTTT      400
    CGAGTTCTTA GTCTTTCTGG AGCTAACTT AAGGAATTGG AGATAATGGT TCAGAGAAAT TGATTTTCGA CCCCTATTAG TATTATCGTG GATTGAAAAA StyI
                                                                                                            SecI
                                                                                                            NcoI
                            BbsI                                                                      AccI  BsaJI
                             ▼                                                                         ▼    ▼
    GGGTACTAAG AAAAGTTAAA TGAAGACTAA ATATATCAGG CACATGGTAA ACAACAAAGA AATCTCATCT ATTTCACTAT TATTAATGTA GACCATGGTC      500
    CCCATGATTC TTTTCAATTT ACTTCTGATT TATATAGTCC GTGTACCATT TGTTGTTTCT TTAGAGTAGA TAAAGTGATA ATAATTACAT CTGGTACCAG ACTCGTGTTA ATAACTTTAA CCTCAACCTT TTAACTGCTA TGAAGGATTA AATAAAAAAT TAATCACTAT ATTATAAAAA TTAATTGATA TATAATAAAT      600
    TGAGCACAAT TATTGAAATT GGAGTTGGAA AATTGACGAT ACTTCCTAAT TTATTTTTTA ATTAGTGATA TAATATTTTT AATTAACTAT ATATTATTTA
```

```
              SnaBI
              BsaAI
         MaeII    PleI                                                    PleI
          ▼▼      ▼                                                        ▼
GAATTTAAGA AATACGTAAT AATTCATGGA CTCCTTGAAG ATAGAAAATT TATACAAAAT CCTAGTAATT TGAGTCACAA AAGCTCCTAC AATAATGAAA    700
CTTAAATTCT TTATGCATTA TTAAGTACCT GAGGAACTTC TATCTTTTAA ATATGTTTTA GGATCATTAA ACTCAGTGTT TTCGAGGATG TTATTACTTT
```

```
                                              DpnI
                                              Sau3AI
                                              MboI
                                              DpnII
                                              BstYI    AlwI
                                              ▼▼       ▼
CAGTATGAAT GAAAAAGAAA AGAAATAACT ATTATATTG GATCTAGCCC ATAATTTTTA ACCAAATGCA CAAAAACAAA CAACAAATAT GAAATTCTCA    800
GTCATACTTA CTTTTTCTTT TCTTTATTGA TAATATAAAC CTAGATCGGG TATTAAAAAT TGGTTTACGT GTTTTTGTTT GTTGTTTATA CTTTAAGAGT
```

```
         BsaBI      EcoRI      DraI        SfaNI
          ▼          ▼          ▼            ▼
CTGTAAAGTG ATTAAAATCA AATTTGAATT CTAAAATTTT AAATTAAATT ATCTAAACAT AATTGATGCA GTTATATGTT TTAATAGGTT TGTTCACAT    900
GACATTTCAC TAATTTTAGT TTAAACTTAA GATTTTAAAA TTTAATTTAA TAGATTTGTA TTAACTACGT CAATATACAA AATTATCCAA ACAAGTGTA
```

```
                          PvuII
                          NspBII         SspI            DraI
                           ▼              ▼               ▼
ATCTGAAATC CAACTCCACA TAGTAGCAGG AACAGCTGGT GTCAGAAATT AAATATTCTT TTAGTCTGGA GTTTTAAAAA ATCAATCTGT TTACTTGAGT   1000
TAGACTTTAG GTTGAGGTGT ATCATCGTCC TTGTCGACCA CAGTCTTTAA TTTATAAGAA AATCAGACCT CAAAATTTTT TAGTTAGACA AATGAACTCA
```

```
                    Bst1107I                                                         HgiAI
                    AccI                      SfaNI                                  Bsp1286I
                      ▼▼                       ▼                                       ▼
AATTTGTTGC TGTTTTCATG GGTGAATTGT ATACAGAAGG ATAGGAATTA TTCTTGGCAT CAAAAGGTCA CTGACTTTCA TATTTAGTGC TCATGGTCTT   1100
TTAAACAACG ACAAAAGTAC CCACTTAACA TATGTCTTCC TATCCTTAAT AAGAACCGTA GTTTTCCAGT GACTGAAAGT ATAAATCACG AGTACCAGAA
```

```
                                               HgiAI
DraI                                           Bsp1286I
 ▼                                              ▼
TAAAAAATGG ATAAAAAGTA GTTCTCACAT TTCATGGAAA GCCCCCAATC CATGAGCACA TTTCCCAAAA TGAAACATT TTTATCAACT GCAAGTTGTG   1200
ATTTTTTACC TATTTTTCAT CAAGAGTGTA AAGTACCTTT CGGGGGTTAG GTACTCGTGT AAAGGGTTTT ACTTTGTAA AAATAGTTGA CGTTCAACAC
```

```
                              MnlI                                                BslI                XmnI
                              ▼                                                    ▼                   ▼
  TGTAGGTGGA GATTTGTTTT TCAATTGTCA AGATACTGTT AATTACCCAG TCCTTTATCT CCTTTTGGTG GAGATGTCTC TGTGCTAGGA AACCCTTCTT  1300
  ACATCCACCT CTAAACAAAA AGTTAACAGT TCTATGACAA TTAATGGGTC AGGAAATAGA GGAAAACCAC CTCTACAGAG ACACGATCCT TTGGGAAGAA
```

```
                              BsrI
                              HaeIII
                              Sau96I                  BspHI               TfiI
                              ▼                        ▼                   ▼
  GCTCTCCTTC CTGTTTCTCT TTTACTACTG GCCCTGAAAC AACAAATTCT CAAGTTTCAT GACACGTTTC CAAAGAATCC ATCAATCAAA TAAGCAACAC  1400
  CGAGAGGAAG GACAAAGAGA AAATGATGAC CGGGACTTTG TTGTTTAAGA GTTCAAAGTA CTGTCGAAAG GTTTCTTAGG TAGTTAGTTT ATTCGTTGTG
```

```
        TaqI                            PacI                 DraI
        ▼                                ▼                    ▼
  AACTCGACAC TGACAATTCC AGACCTACTA AGAGCATTAA TTAAGACTTA AAAATAAACA TGAGTTTTAA AAGGGTGTTA TTCATTATTT TCCCATTTAT  1500
  TTGAGCTGTG ACTGTTAAGG TCTGGATGAT TCTCGTAATT AATTCTGAAT TTTTATTTGT ACTCAAAATT TTCCACAAT AAGTAATAAA AGGGTAAATA
```

```
  MaeII
  ▼
  AACGTCCCTT ACCTTCTGTC CTTCAGTGCA TACAAATTAT TATCTTCCTT GAAGCCCAGT TCAAGCCGTA CCTCACCATG ATACCTTCCA TGTATATTCC  1600
  TTGCAGGGAA TGGAAGACAG GAAGTCACGT ATGTTTAATA ATAGAAGGAA CTTCGGGTCA AGTTCGGCAT GGAGTGGTAC TATGGAAGGT ACATATAAGG
```

```
                                                                                                     NlaIV
                                                                                                     DpnI
                                                                                                     Sau3AI
               StuI                                                                                  MboI
               HaeIII                                                                                DpnII
       ScrFI                                                                                         BstYI
       BstNI                                   NsiI                                          AlwI    BamHI
       ▼▼                                      ▼                                              ▼        ▼▼
  ACTCCAGGCC TCACTGATTT TTAACTGAAA TACTATAATG CATAGTTCAC AATTAAAAAA AAAAAAAACA CAGCACTTTA CATAAGAGCT TACAGGATCC  1700
  TGAGGTCCGG AGTGACTAAA AATTGACTTT ATGATATTAC GTATCAAGTG TTAATTTTTT TTTTTTTTGT GTCGTGAAAT GTATTCTCGA ATGTCCTAGG
```

```
                                                                                             HpaI
   AlwI                                                                                MaeII HincII
   ▼                                                                                    ▼    ▼
  TATTTGTTTT ATCCATTCTT TTGTTCATTT TTACAATCAT TAATTCAAAG GAATTATATT AATTACTTTC TATGCACCCG AAGTGTGTT AACACAACAA  1800
  ATAAACAAAA TAGGTAAGAA AACAAGTAAA AATGTTAGTA ATTAAGTTTC CTTAATATAA TTAATGAAAG ATACGTGGGC TTCACACAA TTGTGTTGTT
```

```
            BsmI            AccI                         SfcI
             ▼               ▼                            ▼
TACTATCCCT GCATTCAGCA AGTCTATGGT CTACAAGAGA GGACACAAAT TCAAATGTCT GTAGTCAAGC AGTGAAGCTG GCTAGATATG GAAAAATTAC   1900
ATGATAGGGA CGTAAGTCGT TCAGATACCA GATGTTCTCT CCTGTGTTTA AGTTTACAGA CATCAGTTCG TCACTTCGAC CGATCTATAC CTTTTTAATG
```

```
                                  DpnI            MboI-RFLP SITE
                                  Sau3aI          (FbaI-RFLP SITE)
                                  MboI
                                  Fba-I
                                  DpnII
                                  BclI                              SfcI
                                   ▼▼                                ▼
AAGTCCCTCT TGCTTTAACA TTTGCTTGCC CACATTGAT CAGACATCAT GCAAAATAAT TTCTCACTAT AGAGAAAAAA ACACTACAAA ACCAATAATA   2000
TTCAGGGAGA ACGAAATTGT AAACGAACGG GTGTAAACTA GTCTGTAGTA CGTTTTATTA AAGAGTGATA TCTCTTTTTT TGTGATGTTT TGGTTATTAT
```

```
                        NsiI
                        NdeI
                        SphI
           BsrI.        NspHI        BspMI                 BspHI     ScaI          NsiI
             ▼           ▼▼           ▼                     ▼         ▼             ▼
TAAAGAACTG AGAACTGGTT TACTGAAGCA TGCATATGTC ATCTAAAAGA AGCAGGTGAC GACCAGCTTC ATGAAGTACT TGCCATGCAT ATTGGCACTT   2100
ATTTCTTGAC TCTTGACCAA ATGACTTCGT ACGTATACAG TAGATTTTCT TCGTCCACTG CTGGTCGAAG TACTTCATGA ACGGTACGTA TAACCGTGAA
```

```
                                                         NheI     FokI    Fnu4HI    BbvI
                                                          ▼        ▼        ▼        ▼
CACACACTGA CCCTTCTCCC CACCTAGACC AGTAATTAAA CAGGTATGGA TGAGCTAGCT ACTAAGAGCA GCCAACTGAA TAGCTGACTA ATTTAGAAGC   2200
GTGTGTGACT GGGAAGAGGG GTGGATCTGG TCATTAATTT GTCCATACCT ACTCGATCGA TGATTCTCGT CGGTTGACTT ATCGACTGAT TAAATCTTCG
```

```
                                                 EspI
                     ScaI                       Bpu1102I                          DraI
                      ▼                           ▼                                ▼
ACACTTGGTA ATAATAGCTG ACTTTTATTA GTACTGACTA TACTATATGC TAAGCTGTAC TCAAAGTGCT TTGAGTTTTA AACTGATACA AACATTATAT   2300
TGTGAACCAT TATTATCGAC TGAAAATAAT CATGACTGAT ATGATATACG ATTCGACATG AGTTTCACGA AACTCAAAAT TTGACTATGT TTGTAATATA
```

```
                                                                            BstUI-RFLP SITE
                                                                                          ╲
                                                                                            HhaI
                                                                                            HinPI
                                                                                            BstUI
                                                                                             ▼▼
GAGGAAACAG AGGTACAGAG AGCTATTCAC CAGCTTACCA AAGGTCACAT AGCTGGTAAG TGGAGGACTT AAACCCAGAC TATCTAGTTT CAGAACGGGC   2400
CTCCTTTGTC TCCATGTCTC TCGATAAGTG GTCGAATGGT TTCCAGTGTA TCGACCATTC ACCTCCTGAA TTTGGGTCTG ATAGATCAAA GTCTTGCCCG
```

```
                                                                                    HgiAI
                                                                                    Bsp1286I
                                                           BslI       ApaLI  SspI
                                                            ▼           ▼ ▼   ▼
AGACTTAATC CATCGTGCAG AACATAAGAC ATACTCCATC TGTCTCCCCA ACTAGGTTAT TATGTGCACA AATATTTATT GGTTGGTTGG TTCATTATTA   2500
TCTGAATTAG GTAGCACGTC TTGTATTCTG TATGAGGTAG ACAGAGGGGT TGATCCAATA ATACACGTGT TTATAAATAA CCAACCAACC AAGTAATAAT
```

```
                                                                     BbsI
     BsrI                                                            XmnI                   NsiI
      ▼                                                              ▼ ▼                     ▼
TGACTGGGTG GTAAGTATGT CATTAGGAGT GTTTTGCTTA TGACTATATA AATTTCTTCA CCAAAAGAAG ACTTTCTGAT GATATACTAT GCATCAGACA   2600
ACTGACCCAC CATTCATACA GTAATCCTCA CAAAACGAAT ACTGATATAT TTAAAGAAGT GGTTTTCTTC TGAAAGACTA CTATATGATA CGTAGTCTGT
```

```
 SfaNI                              XbaI                                  Bsu36I    HindIII
  ▼                                  ▼                                      ▼         ▼
CCACGCAGGG TGCTAAGGTT AGGAAGATAA GTGAGACTTC TAGAAACTCA TTCATTCAAC AAATATCTCC TAAGGGCTAG AAGCTTAGGT TTCAGCAGTG   2700
GGTGCGTCCC ACGATTCCAA TCCTTCTATT CACTCTGAAG ATCTTTGAGT AAGTAAGTTG TTTATAGAGG ATTCCCGATC TTCGAATCCA AAGTCGTCAC
```

```
                         Sau96I
                         AvaII
                          ▼                                                                         BbvI
                                                                                                     ▼
AACAGAATAG GTATGTTCTC TTTGTGTTG GACCTTATAG TATATCTGGG AAAACAGACA TTGAATAAAT ATCACAAATG CAAGTGAGTG TTTCAGAGAC   2800
TTGTCTTATC CATACAAGAG AAACACAAC CTGGAATATC ATATAGACCC TTTTGTCTGT AACTTATTTA TAGTGTTTAC GTTCACTCAC AAAGTCTCTG
```

```
    Fnu4HI
    PvuII
    NspBII
    Fnu4HI
    NspHI        BbvI
    ▼▼▼           ▼
ATGCAGCTGC TACATCAAAC CAAAACAGAA CAAAACAAAC AACCCAAAAA CTGACCAGTG GGATTAAGTG TAAATAGGCA CACAAATGCA CAAATATGCT   2900
TACGTCGACG ATGTAGTTTG GTTTTGTCTT GTTTTGTTTG TTGGGTTTTT GACTGGTCAC CCTAATTCAC ATTTATCCGT GTGTTTACGT GTTTATACGA
```

```
                                                                                        BslI
                                                                                        Bsp1286I
                                                                                  MnlI  BanII
                                                                                   ▼     ▼ ▼
TTTATAAAAT AGTGAAGCAG TGACAGAGAC ACACACAAGA TATAAAGACA CAATGAAGAA CAATTGAGCC CAAAGCTGGA AAGGGTGAGA GTGTGAAGGA   3000
AAATATTTTA TCACTTCGTC ACTGTCTCTG TGTGTGTTCT ATATTTCTGT GTTACTTCTT GTTAACTCGG GTTTCGACCT TTCCCACTCT CACACTTCCT
```

```
     DpnI
     Sau3aI
     MboI
     Fba-I
     DpnII                                   ScrFI
     BclI                                    BstNI         FokI          DraIII
     ▼▼                                      ▼             ▼             ▼
AAAAGGTTGA TCAGAGAAGT TTTCCCGAAG GAGAGAAAGC CTGGATGATT AGGAGGCAAC CACTCGGTGA CTGAGGGAAA TCTGAAAAAT GTATTTGTCA   3100
TTTTCCAACT AGTCTCTTCA AAAGGGCTTC CTCTCTTTCG GACCTACTAA TCCTCCGTTG GTGAGCCACT GACTCCCTTT AGACTTTTTA CATAAACAGT
```

```
                                                                   PflMI
                                                                   BslI      SspI
                                                                   ▼         ▼
TCTTCTCAGA CTGCTGAAG GAATGACTTG GGTACTTTGA GGATTTCAGT AATTTTTCCA TGACTTGGTA TAATATTTCA AAAGGAAATA GGCTGACTTT    3200
AGAAGAGTCT GAACGACTTC CTTACTGAAC CCATGAAACT CCTAAAGTCA TTAAAAAGGT ACTGAACCAT ATTATAAAGT TTTCCTTTAT CCGACTGAAA
```

```
         PleI         TaqI                              SspI                     AflII
         ▼            ▼                                 ▼                        ▼
ATTTGTATAA TGAATGTGAC TCCTTCCTCG ACTGCCATAG AAATAAACTC CTTAATATTT TGGGTTTGTC TTTGCACTTA AGTAATCAGT CATTCTGTTT   3300
TAAACATATT ACTTACACTG AGGAAGGAGC TGACGGTATC TTTATTTGAG GAATTATAAA ACCCAAACAG AAACGTGAAT TCATTAGTCA GTAAGACAAA
```

```
                   SpeI
                   HaeIII                AciI
      PleI         Sau96I       PleI     BbsI  Fnu4HI                     EcoRI
      ▼▼           ▼▼ ▼         ▼        ▼     ▼▼                         ▼
TTTTACAGGG TGACTCTGGT GGCCCACTAG TACAAGAAGA CTCACGGCGG CTTGGTTTA TGTGAAGCC GAATTC                              3376
AAAATGTCCC ACTGAGACCA CCGGGTGATC ATGTTCTTCT GAGTGCCGCC GAACCAAAT AACACTTCGG CTTAAG
           ↑
           |
intron exon
     c    |
           |
           |
           |
```

# ANALYSIS OF PREDISPOSITION BASED ON HUMAN AIRWAY TRYPSIN PROTEASE GENE POLYMORPHISM

This application is the national stage of PCT/JP98/05689, filed Dec. 16, 1998.

TECHNICAL FIELD

This invention relates to a method for predicting the constitution susceptible to the onset of specific diseases, effects on methods of treatment for patients suffering from said diseases or predicting the prognosis of the treatment by analysis of genetic polymorphisms of a human trypsin-like enzyme of a respiratory tract.

BACKGROUND ART

Research on related genes has recently been promoted not only in genetic diseases due to deletion or mutation of single genes but also in multifactorial diseases caused by entanglement of several genetic predispositions and environmental factors. As a result, the deletion or point mutation and isoforms related to the multifactorial diseases and further mutation of genetic parts (introns or promoters) without affecting actually translated amino acid sequences have come to be considered as risk factors for the diseases.

EFFECT OF THE INVENTION

It has been published that the correlation is recognized between bone density and genetic polymorphisms of an intron of the vitamin D receptor in the osteopathic field as the prior art (Morrison, N. A. et al., Nature, 367: 284–287 1994). In the field of circulatory organs, it has been reported that the I type (insertion type) and D type (deletion type) genetic polymorphisms of an angiotensin-converting enzyme are associated with the onset of myocardial infarctions (Cambien, F. et al., Nature 359: 641–644, 1992) and the amino acid substitution of M295T of angiotensinogen and the polymorphisms of a promoter region of G-6A are associated with the onset of essential hypertension (Inoue, I. et al., J. Clin. Invest., 99: 1786–1797, 1997). Furthermore, in the field of the nervous system, it has been reported on the association between the onset of dementia and the isoforms of apoE protein. Much research has been carried out in the association between the genetic polymorphisms of glutathione S-transferase and the onset of cancers in the cancer-related field. As the field of respiratory diseases, it has been reported on the association between the onset or morbid state of asthma and the TNF (Moffatt, M. F. et al., Hum. Mol. Genet. 6 (4): 551–554, 1997) and the association between the onset or morbid state of the asthma and the genetic polymorphisms of an angiotensin converting enzyme (Benessiano, J. et al., J. Allergy Clin. Immunol. 99 (1): 53–57, 1997).

Furthermore, attention has been paid to the genetic background as one of causes of difference between patients in sensitivity to drugs used for treating diseases, and it is has been desired even by the medical site to provide the directionality such as selection of methods of treatment according to the drug sensitivity of individual humans by diagnosis of the genetic polymorphisms. It is thought that the drug development by selecting patient groups expectable of drug effects according to the genetic polymorphisms is effective in clinical trials (Kleyn K. W. et al., Science, 281: 1820–1821, 1998). A report on the genetic polymorphisms of an intron of an angiotensin converting enzyme [ACE (angiotensin converting enzyme)] and effects of an ACE inhibitor (Yoshida, H. et al., J. Clin. Invest. 96: 2162–2169, 1995), a report on the genetic polymorphisms of beta 2-adrenergic receptor and effects of the beta-agonist on asthma (Liggett, S. B., Am. J. Respir. Crit. Care Med. 156 (4 Pt 2): S156–162, 1997) and the like are cited as the conventional reports related to the drug sensitivity and the genetic polymorphisms.

On the other hand, the human trypsin-like enzyme of the respiratory tract related to the present invention has been purified from the sputum of patients suffering from chronic airway diseases (Japanese Unexamined Patent Publication No. 7-067640 and Yasuoka, S. et al., Am. J. Respir.Cell Mol. Biol., 16: 300–308, 1997) and the amino acid sequence and cDNA sequence thereof have been already made clear (Japanese Unexamined Patent Publication No. 8-89246 and Yamaoka K. et. al., J. Biol. Chem., 273(19): 11895–11901, 1998). Several studies have been made of the activity possessed by the enzyme in vitro. Since the enzyme has production enhancing actions on cytokines such as IL-8 or GM-CSF derived from a human bronchial epithelial cell line including the association with mucociliary movement, the possibility for association with the morbid state of airway inflammations is considered (Terao, Noriko et al., the Japanese Respiratory Society, 1998). Since the enzyme has enzyme activities such as hydrolytic activity for fibrinogen and activating actions on plasminogen activators (pro-urokinase) (Yoshinaga, Junko et al., Conference on Proteases and Inhibitors in Pathophysiology and Therapeutics, 1998), the possibility is assumed for anti-inflammatory actions through the formation of fibrins on the airway mucosal surfaces or modification of the morbid state thereof in chronic airway diseases and the possibility is also considered for the association with cancer metastasis or the like. The association of the enzyme with physiological functions or the morbid state in vivo is not yet sufficiently elucidated, and the genetic parts (introns or promoters) without corresponding to the actually translated amino acid sequences has not yet known about genes at all. Further, no investigation has hitherto been carried out on the association of the presence or absence of the genetic polymorphisms for the human trypsin-like enzyme of the respiratory tract or the genetic polymorphisms with diseases.

By the way, much information can be provided about the prediction of the onset of specific diseases, prognosis of treatment, selection of appropriate methods of the treatment and administered drugs or the like by the prediction of diseases-associated constitution by genetic analysis. Accordingly, the prediction is desired by many physicians and patients and further makes the prophylaxis of onset and early therapy possible. Therefore, it is thought that the prediction is related with a reduction in medical care expenditures to become indispensable for the future medical care.

It is, however, very difficult to find out a gene associated with diseases and establish an analytical method therefor, and there are few examples of genetic analytical methods in which the association with diseases is recognized as described above. Therefore, the development of the genetic analytical technique for making various disease-associated constitutions predictable is strongly desired.

On the other hand, it is not yet elucidated with what diseases the human trypsin-like enzyme of the respiratory tract is associated at present.

DISCLOSURE OF THE INVENTION

As a result of intensive research made in consideration of the problems of the prior art, the present inventors et al. have designed a primer for genetically amplifying an intron part on the genome of the human trypsin-like enzyme of the respiratory tract specifically expressing in the human respiratory tract, novelly determined the DNA sequence of both the termini of the amplified genetic fragment and the novelly determined DNA sequence in an exonlintron border part, found out that there are genetic polymorphisms in the amplified genetic fragment and the novelly determined DNA sequence and further firstly found out the association of the genotypes of the human trypsin-like enzyme of the respiratory tract with diseases in individual humans by analyzing the genetic polymorphisms, thus attaining the present invention.

That is, an object of the present invention is to provide a method for predicting the constitution of individual humans susceptible to the onset of specific diseases or effects of treatment on patients or prognosis of the treatment by analyzing the genetic polymorphisms of the human trypsin-like enzyme of the respiratory tract.

Further, the present invention is a method for diagnosing an abnormality in the mucociliary biophylactic system by the analysis of the genetic polymorphisms of the human trypsin-like enzyme of the respiratory tract and a method for predicting the constitution of individual humans susceptible to the onset of diseases, effects of treatment on patients or prognosis of the treatment.

Furthermore, the present invention is a genetic fragment containing a part or all of the base sequence of an intron in the human trypsin-like enzyme of the respiratory tract.

BRIEF DESCRIPTION OF DRAWINGS

FIG. 4 illustrates the nucleic acid sequence of intron C (SEQ ID NO: 17), designates the location of 5' and 3' boundaries of the intron, and indicates the specification restriction endonuclease recognition sites in intron C.

BEST MODE FOR CARRYING OUT THE INVENTION

Figure 1:
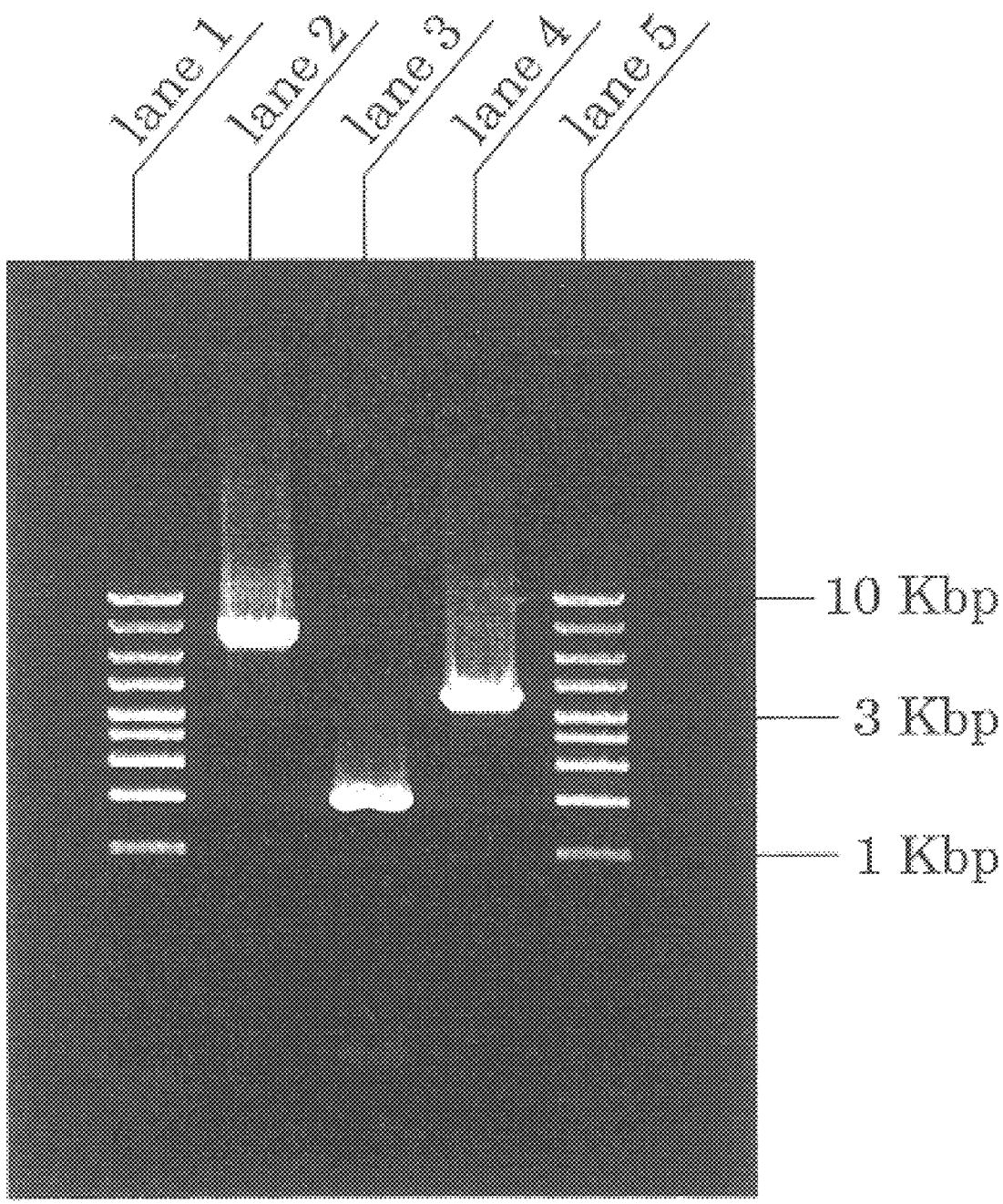
FIG. 1 illustrates agarose gel electrophoretic patterns of DNA fragments containing an intron region of a gene encoding a mature protein of the human trypsin-like enzyme of the respiratory tract obtained by genetic amplification. It is observed that lanes 1 and 5 are markers (10 Kb, 7 Kb, 5 Kb, 4 Kb, 3 Kb, 2.5 Kb, 2 Kb, 1.5 Kb and 1 Kb from above), lane 2 is a DNA fragment of about 6 Kb amplified by primers A1 (SEQ ID NO: 7) and A2 (SEQ ID NO: 8), lane 3 is a DNA fragment of about 1.5 Kb amplified by primers B1 (SEQ ID NO: 9) and B2 (SEQ ID NO: 10) and lane 4 is a DNA fragment of about 3.4 Kb amplified by primers C1 (SEQ ID NO: 11) and C2 (SEQ ID NO: 12).

According to the present invention, there are provided a method for predicting the association of the constitution of individual humans with specific diseases and a genetic fragment or a DNA sequence used for the genetic analysis thereof.

Respiratory diseases, pulmonary cancer, especially pulmonary emphysema (PE), sinobronchial syndrome, diffuse panbronchiolitis (DPB) and bronchiectasis (BE) belonging to chronic obstructive pulmonary diseases (COPD) or abnormalities in the mucociliary biophylactic system are exemplified as specific diseases for judging the constitution susceptible to the onset or specified diseases for predicting the judgment on effects of treatment thereof or prognosis of the treatment by the method of the present invention.

Analysis of the genotypes classified by detecting one or more base mutations and analysis of the haplotypes classified by detecting one or more of the base mutations are exemplified as an analytical method for the genetic polymorphisms of the human trypsin-like enzyme of the respiratory tract in the present invention.

The analytical method for the genetic polymorphisms of the trypsin-like enzyme of the respiratory tract is carried out by, for example, an analytical method by a restriction fragment length polymorphisms (RFLP) according to the cleavage with a restriction enzyme. The analytical method for the genetic polymorphisms in the present invention includes even an analytical method for the genetic polymorphisms detectable by the Southern hybridization using a cDNA sequence of the human trypsin-like enzyme of the respiratory tract. That is, it is a method for cleaving the genomic DNA with a restriction enzyme capable of detecting the genetic polymorphisms disclosed in the present invention, then carrying out a gel electrophoresis, performing transcription to a nitrocellulose membrane or the like and subsequently analyzing the cleaved patterns of the human trypsin-like enzyme genome of the respiratory tract using the human trypsin-like enzyme cDNA of the respiratory tract as a probe. The analysis can be made even by a method for amplifying a DNA fragment by PCR so as to include sites for the genetic polymorphisms, then converting the amplified DNA fragment into a single strand and analyzing the resulting single strand by a difference in mobility of electrophoresis [PCR-single strand conformation polymorphism (SSCP)] method or the like. Furthermore, many methods such as a mismatch PCR method, a PCR-allele specific oligo (ASO) method using an allele specific oligonucleotide, a method for judgment by carrying out annealing using an oligo probe or a pinpoint sequencing method for directly determining the base sequence of the genetic polymorphic sites are cited as the method for making the detection of the polymorphic sites possible, and the analytical method for the genetic polymorphisms can be applied even to genetic diagnosis by using a DNA chip.

An intron may be used as sites for analysis of the genetic polymorphisms, and the following genetic fragments are exemplified as the site for analysis of the specific genetic polymorphisms:

(a) a genetic fragment containing an intron region amplifiable by using the primers represented by SEQ ID NO: 7 and SEQ ID NO: 8, (b) a genetic fragment containing an intron region amplifiable by using the primers represented by SEQ ID NO: 9 and SEQ ID NO: 10, (c) a genetic fragment containing an intron region amplifiable by using the primers represented by SEQ ID NO: 11 and SEQ ID NO: 12, (d) a genetic fragment containing an intron region amplifiable by using the primers represented by SEQ ID NO: 13 and SEQ ID NO: 14, (e) a genetic fragment containing an intron region amplifiable by using the primers represented by SEQ ID NO: 15 and SEQ ID NO: 16, (f) a genetic fragment containing intron C amplifiable by using the primers represented by SEQ ID NO: 11 and SEQ ID NO: 12, and (g) a genetic fragment containing intron A amplifiable by using the primers represented by SEQ ID NO: 7 and SEQ ID NO: 8.

In the intron C, a genetic fragment containing a sequential part recognized herein by a restriction enzyme BstUI, MboI, MseI or FbaI is exemplified as the sites for analysis of the genetic polymorphisms. In the intron A, a part containing a sequential part recognized by a restriction enzyme MboI, TaqI or AfaI, one of the genetic polymorphic sites represented by SEQ ID NO: 17 or a combination of one or more thereof is exemplified as the sites for the analysis of the genetic polymorphisms. The genotypic or haplotypic classification is judged by the analysis of the sites.

Furthermore, the present invention is a genetic fragment containing a part or all of the base sequence of an intron in the human trypsin-like enzyme of the respiratory tract and the following genetic fragments are especially exemplified:

(a) a genetic fragment containing an intron region amplifiable by using the primers represented by SEQ ID NO: 7 and SEQ ID NO: 8, (b) a genetic fragment containing an intron region amplifiable by using the primers represented by SEQ ID NO: 9 and SEQ ID NO: 10, (c) a genetic fragment containing an intron region ampliflable by using the primers represented by SEQ ID NO: 11 and SEQ ID NO: 12, (d) a genetic fragment containing an intron region amplifiable by using the primers represented by SEQ ID NO: 13 and SEQ ID NO: 14, (e) a genetic fragment containing an intron region amplifiable by using the primers represented by SEQ ID NO: 15 and SEQ ID NO: 16, (f) a genetic fragment containing an intron in the human trypsin-like enzyme of the respiratory tract comprising the base sequence represented by any of SEQ ID NOS: 1–6 or a genetic fragment sandwiched between the base sequences, and (g) a genetic fragment of the intron C in the human trypsin-like enzyme of the respiratory tract comprising the base sequence represented by SEQ ID NO: 17.

EXAMPLES

The present invention is explained in detail hereinafter by way of examples, provided that the examples are not intended as a definition of the method for predicting the disease-associated constitution by the analysis of the genetic polymorphisms of the human trypsin-like enzyme of the respiratory tract.

Standard Methods for Operations

Standard DNA extracting operations, genetic amplifying operations, restriction enzyme cleavage operations and electrophoretic operations usable in the present invention are explained hereinafter.

(a) Standard DNA Extracting Operations

Nothing is especially limited in biosamples used for the genetic amplification of the present invention; however, blood corpuscle components are suitable because specimens are readily collected and DNA is easily extracted.

1. The whole blood in a volume of 0.5 ml (using a 2Na-EDTA anticoagulant) is placed in a microcentrifugal tube having a capacity of 1.5 ml.

2. A dissolvent in a volume of 0.5 ml is added to the tube, and the tube is lightly tapped several times. The tube is then turned upside down, and the liquids are mixed.

(The following mixing operations are performed according to the above procedures).

An example of the dissolvent: 1×SSC

This is prepared by diluting 20×SSC regulated to pH 7.0 with 10N NaOH containing 175.3 grams of NaCl and 88.2 grams of sodium citrate in 1 liter 10-fold.

3. The mixture is centrifuged (at 4° C. and 10,000 g for 20 seconds), and the supernatant is then removed so as not to discharge dark pellets.

4. The dissolvent in a volume of 1 ml is added to stir the mixture

5. The mixture is centrifuged (at 4° C. and 10,000 g for 20 seconds), and the supernatant is then removed.

6. Steps 4 and 5 are repeated once more.

7. An enzyme reaction solution in a volume of 200 $\mu$l and a proteolytic enzyme in a volume of 10 $\mu$l are added and mixed therewith. An example of the enzyme reaction solution: A mixture liquid of 0.04 M DTT (dithiothreitol) with 0.2 M NaOAc (sodium acetate) and 0.4%SDS An example of the proteolytic enzyme liquid:

A 10 mg/ml proteinase (Proteinase K)

8. The mixture is kept warm at 37° C. for 1 hour (the mixture is mixed by lightly shaking 2 to 3 times in the course thereof).

9. A solution of sodium iodide in a volume of 300 $\mu$l is added and mixed therewith.

10. Isopropyl alcohol in a volume of 0.5 ml is added and mixed until a white linear DNA is completely visible.

11. The resulting mixture is centrifuged (at room temperature and 10,000 g for 10 minutes), and the supernatant is then slowly removed. The solution remaining in a tube wall is sufficiently removed by a method for placing the tube on a filter paper upside down or the like.

12. A wash liquid (A) in a volume of 1 ml is added and mixed therewith. The mixture is sufficiently mixed so as to peel a precipitate from the tube wall.

An example of the wash liquid (A): 70% EtOH

13. The resulting mixture is centrifuged (at room temperature and 10,000 g for 5 minutes), and the supernatant is then removed.

14. A wash liquid (B) in a volume of 1 ml is added, and the prepared mixture is sufficiently mixed so as to peel the precipitate from the tube wall.

An example of the wash liquid (B): 80% EtOH

15. The mixture is centrifuged (at room temperature and 10,000 g for 5 minutes), and the supernatant is then removed.

16. The DNA precipitate is lightly vacuum-dried (the drying time is within 3 minutes because the DNA is sparingly dissolved when drying the precipitate too much).

(a) Standard Genetic Amplifying Operations

Although several principles are known about the genetic amplifying method, the polymerase chain reaction method (PCR method) is described as a standard one hereinafter.

Composition of the reaction solution: 50 mM of KCl, 10 mM of Tris-HCl (pH 9.0, 25° C.), 0.1% of TritonX-100, 1.5 mM of $MgCl_2$, 2 mM of dNTPs, 15 $\mu$M of Forward Primer, 15 $\mu$M of Reverse Primer, 1 mg/l of a genomic DNA and 1 unit of TaqDNA polymerase, the total volume of 50 $\mu$l Reaction cycle: at 94° C. for 1 minute, 64° C. for 1 minute and 72° C. for 1 minute as one cycle. The reaction is conducted for 40 cycles.

Primers used are the following C1 (35 bases) and C2 (35 bases):

C1: 5'-GGAGC CATCT TGTCT GGAAT GCTGT GTGCT GGAGT-3' (SEQ ID NO: 11)

C2: 5'-CACAA TAAAC CAAAG CCGCC GTGAG TCTTC TTGTA-3' (SEQ ID NO: 12)

(c) Standard Restriction Enzyme Cleavage Operations

Composition of the reaction solution for MboI: 10 mM of Tris-HCl (pH7.4), 10 mM of $MgCl_2$, 100 mM of NaCl, 10 mM of KCl, 1 mM of DTT and 100 μg/ml of BSA (bovine serum albumin)

MboI at a concentration of 10 units/20 μl of reaction solution is added to carry out incubation at 37° C. for 3 hours.

(b) Standard Electrophoretic Operations

The buffer solution for electrophoresis is 0.5×TBE, with the proviso that 5×TBE contains 54 grams of Tris base, 27.5 grams of boric acid and 1 mM of EDTA in 1 liter and is regulated to pH 8.0. The above buffer solution is used to carry out electrophoresis under a voltage of 100 V for 30 minutes by using a 1% or a 3% agarose gel [using Seakem GTA Agarose (FMC Bio Products)] (containing 0.5 μl/ml of ethydium bromide). The band of the DNA is then observed with a UV lamp.

Example 1

Obtaining of DNA Fragment Containing an Intron on Human Trypsin-like Enzyme Genome of the Respiratory Tract and Analysis of Base Sequence Thereof In order to search for an intron site on the genome of a mature human trypsin-like enzyme of the respiratory tract, primers were prepared by referring to the constitution of exons and introns of the genome of several typtase analogous enzymes to amplify a human genomic DNA. A DNA fragment (genetic fragment) of about 6 KB was amplified by the primers A1 (SEQ ID NO: 7) and A2 (SEQ ID NO: 8), and a DNA fragment of about 1.5 Kb was amplified by the primers B1 (SEQ ID NO: 9) and B2 (SEQ ID NO: 10). A DNA fragment of about 3.4 Kb was amplified by the primers C1 (SEQ ID NO: 11) and C2 (SEQ ID NO: 12). (FIG. 1)

The DNA fragments were excised from gels and purified, and the respective fragments were inserted into TA cloning vectors (manufactured by Invitrogen Corporation). The base sequences on both sides (5'-terminus and 3'-terminus) of the insert DNA were determined for several clones thereof to find that the cDNA sequence of the human trypsin-like enzyme of the respiratory tract was present contiguous to the sequences of the primers, consensus sequences were recognized as contiguous thereto in border regions of the exon-intron on both sides of the 5'-terminus and the 3'-terminus and the amplified DNA fragment was a DNA fragment containing the intron region in the human trypsin-like enzyme of the respiratory tract.

Figure 3:
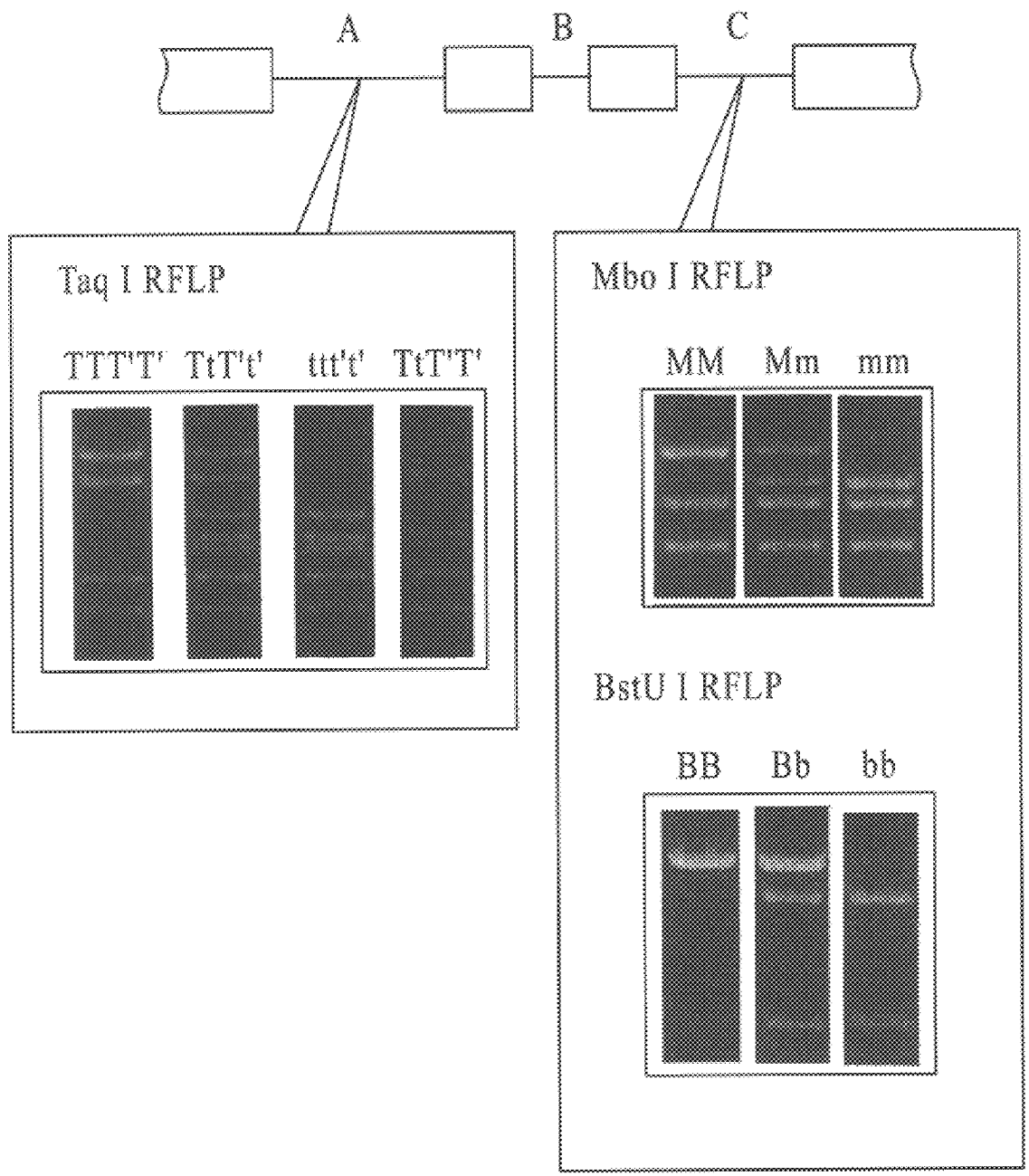
FIG. 3 illustrates relative positions of introns A, B and C on the human trypsin-like enzyme genome of the respiratory tract and agarose gel electrophoretic patterns of genetic polymorphisms (RFLP) of the intron A detected by TaqI and of the intron C detected by MboI and BstUI.

The sequences of the introns which have been made clear in the present invention in a genetic region encoding the mature protein of the human trypsin-like enzyme of the respiratory tract are respectively referred to as intron A, intron B and intron C from the 5'-side. (FIG. 3). The base sequences at the 5'- and 3'-termini of the clarified respective introns are as represented by SEQ ID NOS: 1, 2, 3, 4, 5 and 6. As for the intron C, the whole base sequence is represented by SEQ ID NO: 17.

Figure 2:
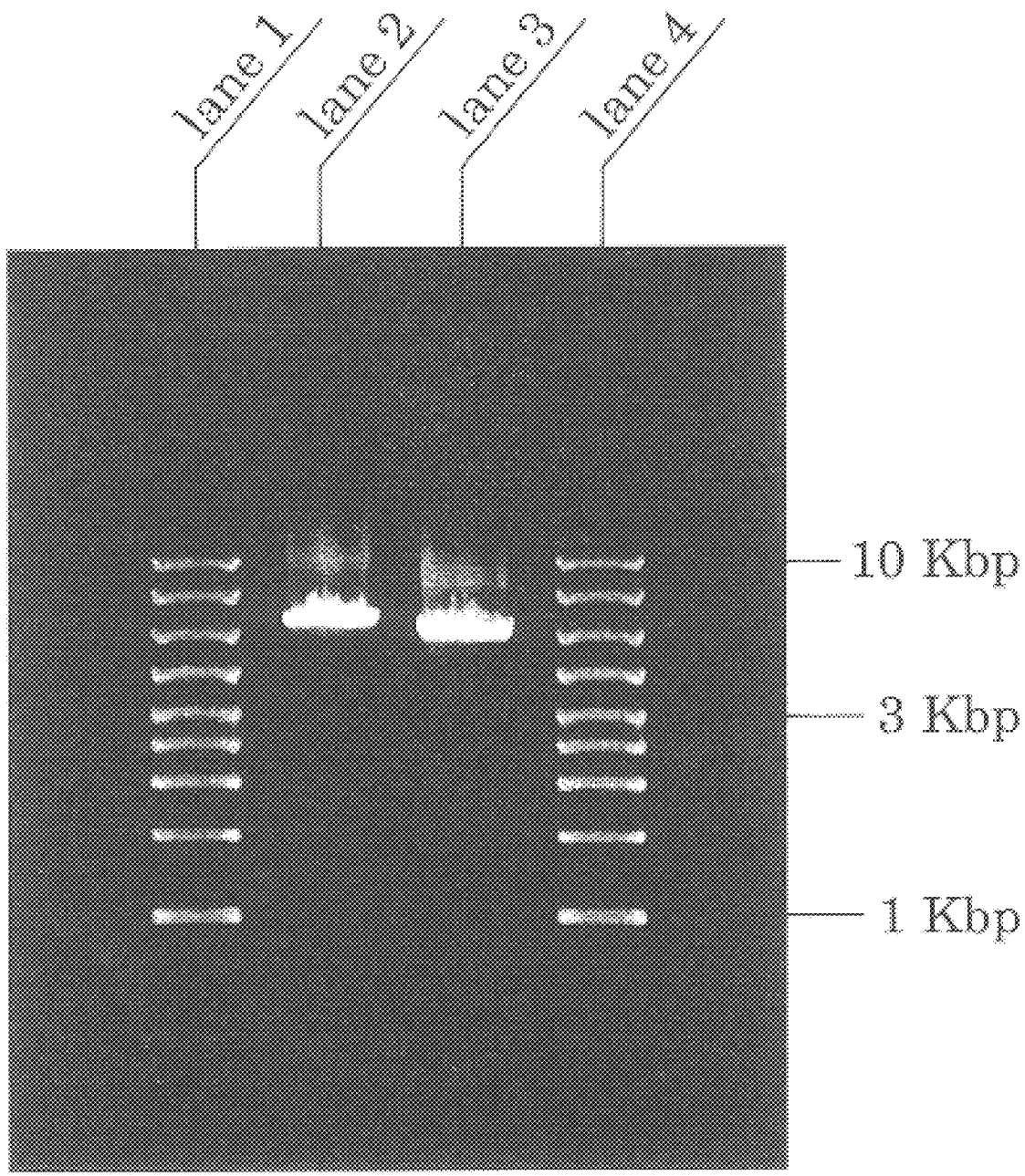
FIG. 2 illustrates agarose gel electrophoretic patterns of DNA fragments containing an intron region of a gene encoding a propeptide of the human trypsin-like enzyme of the respiratory tract obtained by genetic amplification. It is observed that lanes 1 and 4 are markers (10 Kb, 7 Kb, 5 Kb, 4 Kb, 3 Kb, 2.5 Kb, 2 Kb, 1.5 Kb and 1 Kb from above), lane 2 is a DNA fragment of about 5.5 Kb amplified by primers D1 (SEQ ID NO: 13) and D2 (SEQ ID NO: 14) and lane 3 is a DNA fragment of about 5 Kb amplified by primers E1 (SEQ ID NO: 15) and E2 (SEQ ID NO: 16).

On the other hand, several primers were prepared for the region encoding a propeptide of the human trypsin-like enzyme of the respiratory tract to carry out the genetic amplification. Thereby, it was clear that a DNA fragment of about 5.5 Kb was amplified by the primers D1 (SEQ ID NO: 13) and D2 (SEQ ID NO: 14) and a DNA fragment of about 5 Kb was amplified by the primers E1 (SEQ ID NO: 15) and E2 (SEQ ID NO: 16). (FIG. 2). The genetic fragments are regarded as containing the introns.

Example 2

Analysis of Genetic Polymorphisms of Introns in Human Trypsin-like Enzyme of the Respiratory Tract In order to investigate whether or not the genetic polymorphisms are present in the introns A, B and C, the genomic DNA of normal 23 humans was extracted from the whole blood (the standard method for operations) and respectively amplified by the primers A1 and A2 for amplifying the intron A, the primers B1 and B2 for amplifying the intron B and the primers C1 and C2 for amplifying the intron C according to the PCR to compare the cleavage patterns with various kinds of restriction enzymes. As a result, it was found that the genetic polymorphisms were observed with the restriction enzymes MboI, TaqI and AfaI in the intron A. Conversely, the genetic polymorphisms were not observed by restriction enzymes Tsp509I, AluI, NlaIII, MspI, BstUI, BfaI, HinPI, HaeIII, HindIII, SspI, PstI, EcoRI, SalI and EcoRV.

In the intron B, the genetic polymorphisms were not observed by the restriction enzymes Tsp509I, AluI, NlaIII, MspI, BstUI, BfaI, HinPI, HaeIII, MboI, AfaI, TaqI, MseI, ClaI, NsiI, EcoT14I, NdeI, PmlI, ApaLI, AatII, ApaI, KpnI, BsmI, HindIII, SspI and EcoRV.

In the intron C, it was found that the genetic polymorphisms were observed by the restriction enzymes MboI, BstUI, MseI and FbaI. Conversely, the genetic polymorphisms were not observed by restriction enzymes AluI, NlaIII, MspI, BfaI, HinPI, HaeIII, AfaI, TaqI, HindIII, SspI, BglII, EcoT14I, PvuII, PvuI, EcoRI, BamHI, EcoRV and KpnI.

When the DNA fragment containing the intron C amplified by using a combination of the primers C1 and C2 was cleaved with the MboI or BstUI, experiments on cleavage by the MboI revealed that the case where a band appeared at 1.3 Kb could be judged as genotype MM, the case where a band appeared at 1.05 Kb could be judged as genotype mm and the case where two bands appeared together at 1.3 Kb and 1.05 Kb could be judged as genotype Mm according to the electrophoresis. On the other hand, in the case of the BstUI, the case where a band appeared at 3.4 Kb could be judged as BB, the case where two bands appeared at 2.45 Kb and 0.95 Kb could be judged as bb and the case where three bands appeared together could be judged as Bb.

FIG. 3 shows electrophoretic patterns of the genetic polymorphisms of the intron A detected by TaqI, and of the intron C detected by MboI and BstUI. Furthermore, the whole base sequence of the bm type haplotype was determined for the intron C from the DNA fragment obtained from the genome of one example of a bbmm type normal human by PCR (SEQ ID NO: 17) The genetic polymorphic sites detected by BstUI and MboI in the base sequence of the intron C are indicated by arrows with white spaces.

The base sequence of one example of a patient suffering from the BBmm type BE was determined to find that the base sequence of the Bm haplotype BstUI genetic polymorphic sites were not cleaved with the BstUI because CGCG was converted into ACCG.

Example 3

Analysis of Disease-associated Constitution by the Analysis of the Intron Genetic Polymorphisms of Human Trypsin-like Enzyme of the Respiratory Tract As for the statistical analysis, the analysis was made according to the chi-square test using a statistical analysis software Stat View4.02 (Abacus Concepts Co.).

Example 3-1

Analysis of Disease-associated Constitution by Genotypic Classification

Among the genotypes disclosed in Example 2, investigation was made whether or not the classification of diseases associated with the human trypsin-like enzyme of the respiratory tract can be made for the genetic polymorphisms detected with the MboI and BstUI in the intron C. The diseases selected as objects are diffuse panbronchiolitis (DPB), bronchiecstasis (BE), pulmonary emphysema (PE) and bronchial asthma (BA) which are respiratory diseases.

The genotypes of each human were judged by selecting 106 normal humans, 29 patients suffering from the diffuse panbronchiolitis (DPB), 38 patients suffering from the bronchiecstasis (BE), 22 patients suffering from pulmonary emphysema (PE) and 32 patients suffering from the bronchial asthma (BA) according to the standard method for operations. MboI and BstUI were used as the restriction enzymes.

The number of humans having the occurrence and the frequency of occurrence of each genotype and the number of occurrence and the frequency of occurrence of each allelic type were as shown in Tables 1 and 2.

TABLE 1

BstUI genotype

| | Number of humans having the occurrence (humans) | | | | Number of occurrence (allele) | | | |
|---|---|---|---|---|---|---|---|---|
| | BB | Bb | bb | Total | | B | b | Total |
| Normal | 16 | 55 | 35 | 106 | Normal | 87 | 125 | 212 |
| DPB | 8 | 12 | 9 | 29 | DPB | 28 | 30 | 58 |
| BE | 11 | 15 | 12 | 38 | BE | 37 | 39 | 76 |
| PE | 5 | 12 | 5 | 22 | PE | 22 | 22 | 44 |
| BA | 2 | 12 | 18 | 32 | BA | 16 | 48 | 64 |

| | Frequency of occurrence (%) | | | | Frequency of occurrence (%) | |
|---|---|---|---|---|---|---|
| | BB | Bb | bb | | B | b |
| Normal | 15.1 | 51.9 | 33.0 | Normal | 41.0 | 59.0 |
| DPB | 27.6 | 41.4 | 31.0 | DPB | 48.3 | 51.7 |
| BE | 28.9 | 39.5 | 31.6 | BE | 48.7 | 51.3 |
| PE | 22.7 | 54.5 | 22.7 | PE | 50.0 | 50.0 |
| BA | 6.3 | 37.5 | 56.3 | BA | 25.0 | 75.0 |

TABLE 2

MboI genotype

| | Number of humans having the occurrence (humans) | | | | Number of occurrence (allele) | | | |
|---|---|---|---|---|---|---|---|---|
| | MM | Mm | mm | Total | | M | m | Total |
| Normal | 10 | 40 | 56 | 106 | Normal | 60 | 152 | 212 |
| DPB | 3 | 7 | 19 | 29 | DPB | 13 | 45 | 58 |
| BE | 3 | 15 | 20 | 38 | BE | 21 | 55 | 76 |
| PE | 3 | 6 | 13 | 22 | PE | 12 | 32 | 44 |
| BA | 1 | 12 | 19 | 32 | BA | 14 | 50 | 64 |

| | Frequency of occurrence (%) | | | | Frequency of occurrence (%) | |
|---|---|---|---|---|---|---|
| | MM | Mm | mm | | M | m |
| Normal | 9.4 | 37.7 | 52.8 | Normal | 28.3 | 71.7 |
| DPB | 10.3 | 24.1 | 65.5 | DPB | 22.4 | 77.6 |
| BE | 7.9 | 39.5 | 52.6 | BE | 27.6 | 72.4 |
| PE | 13.6 | 27.3 | 59.1 | PE | 27.3 | 72.7 |
| BA | 3.1 | 37.5 | 59.4 | BA | 21.9 | 78.1 |

Tables 1 and 2 show that the frequency of occurrence of BB type manifests a higher tendency in the DPB, BE and PE by judging the above genotypes. That is, the judgment can be made that individual humans having the genotypes have constitutions susceptible to the DPB, BE and PE. Furthermore, when the DPB, BE and PE are collected into the patient groups suffering from the respiratory three diseases according to the classification of the chronic obstructive pulmonary diseases (COPD), results are obtained as follows: The frequency of occurrence of the BB type is statistically significantly higher than that of normal humans (chi-square p value=0.04 and chi-square value=4.2).

| | BB | NotBB | Total |
|---|---|---|---|
| | Frequency of observation Three diseases, BB/NotBB | | |
| Normal | 16 | 90 | 106 |
| Respiratory 3 diseases | 24 | 65 | 89 |
| | — | — | — |
| Total | 40 | 155 | 195 |
| | Percent (row): Three diseases, BB/Not BB | | |
| Normal | 15 | 85 | 100 |
| Respiratory 3 diseases | 27 | 73 | 100 |
| | — | — | — |
| Total | 21 | 79 | 100 |

| Contingency table analytical statistics: Three diseases, BB/NotBB | |
|---|---|
| Number of missing values | 63 |
| Degree of freedom | 1 |
| Chi-square value | 4.182 |
| Chi-square p value | .0409 |
| G-square value | 4.177 |
| G-square p value | .0410 |
| Contingency table analytical coefficient | .145 |
| Phi | .146 |

-continued

| Contingency table analytical statistics: Three diseases, BB/NotBB | |
|---|---|
| Chi-square value (Yates' continuity correction) | 3.489 |
| Chi-square p value (Yates' continuity correction) | .0618 |
| Fisher's direct method p value | .0503 |

Example 3-2

Analysis of Disease-related Constitution by Haplotypic Classification
Frequency of Occurrence of Haplotypes The number of humans having the occurrence and the frequency of occurrence of the haplotypes according to a combination of both genetic polymorphisms of BstUI and MboI in 106 normal humans, 29 patients suffering from diffuse panbronchiolitis (DPB), 38 patients suffering from bronchiectasis (BE), 22 patients suffering from pulmonary emphysema (PE) and 32 patients suffering from bronchial asthma (BA) are shown in the tables. As a result of investigation on 238 humans, the tables suggest that the bM haplotype is almost absent in Japanese due to the absence of anyone having the genotypes of Bb-MM, bb-MM and bb-Mm at all.

to find that there was a deviation in distribution of the frequency of occurrence between the respiratory three disease groups (DPB, BE and PE) belonging to the COPD and normal humans with a statistical significant difference (p=0.027). Particularly, the frequency of occurrence of Bm allele was higher in the respiratory three disease groups (DPB, BE and PE) belonging to the COPD than in normal humans.

The frequency of occurrence of Bm allele in the BE, DPB and PE was high with regard to each disease.

Conversely, the frequency of occurrence of Bm allele was lower for the BA.

| | Frequency of observation: Three diseases, allele | | | |
|---|---|---|---|---|
| | Bm. | BM | b.m. | Total |
| Normal | 27 | 60 | 125 | 212 |
| Respiratory 3 diseases | 41 | 46 | 91 | 178 |
| | — | — | — | — |
| Total | 68 | 106 | 216 | 390 |

| | Number of humans having the occurrence (humans) | | | | | | | | |
|---|---|---|---|---|---|---|---|---|---|
| | BB-MM | BB-Mm | BB-mm | Bb-MM | Bb-Mm | Bb-mm | bb-MM | bb-Mm | bb-mm | Total |
| Normal | 10 | 6 | 0 | 0 | 34 | 21 | 0 | 0 | 35 | 106 |
| DPB | 3 | 2 | 3 | 0 | 5 | 7 | 0 | 0 | 9 | 29 |
| BE | 3 | 7 | 1 | 0 | 8 | 7 | 0 | 0 | 12 | 38 |
| PE | 3 | 0 | 2 | 0 | 6 | 6 | 0 | 0 | 5 | 22 |
| BA | 1 | 1 | 0 | 0 | 11 | 1 | 0 | 0 | 18 | 32 |

| | Frequency of occurrence (%) | | | | | | | | |
|---|---|---|---|---|---|---|---|---|---|
| | BB-MM | BB-Mm | BB-mm | Bb-MM | Bb-Mm | Bb-mm | bb-MM | bb-Mm | bb-mm | Total |
| Normal | 9.4 | 5.7 | 0.0 | 0.0 | 32.1 | 19.8 | 0.0 | 0.0 | 33.0 | 100% |
| DPB | 10.3 | 6.9 | 10.3 | 0.0 | 17.2 | 24.1 | 0.0 | 0.0 | 31.0 | 100% |
| BE | 7.9 | 18.4 | 2.6 | 0.0 | 21.1 | 18.4 | 0.0 | 0.0 | 31.6 | 100% |
| PE | 13.6 | 0.0 | 9.1 | 0.0 | 27.3 | 27.3 | 0.0 | 0.0 | 22.7 | 100% |
| BA | 3.1 | 3.1 | 0.0 | 0.0 | 34.4 | 3.1 | 0.0 | 0.0 | 56.3 | 100% |

As for the following analysis, the statistical technique (chi-square method) was used to promote the analysis of the association with respiratory diseases on the assumption that the human trypsin-like enzyme of the respiratory tract genetic haplotypes of Japanese were the three kinds of BM, Bm and bm (when the number of occurrence was 5 or more, the chi-square p values were used as the following p values and the Fisher's direct method p values were indicated as the following p values in the case of 2×2 table including a frame of the number of occurrence of 4 or below).
Allelic Classification (1)
The investigation was made on the frequency of occurrence of each allele for three kinds of haplotypes of Japanese

| | Percent (row): Three diseases, allele | | | |
|---|---|---|---|---|
| | Bm. | BM | b.m. | Total |
| Normal | 13 | 28 | 59 | 100 |
| Respiratory 3 diseases | 23 | 26 | 51 | 100 |
| | — | — | — | — |
| Total | 17 | 27 | 55 | 100 |

| Contingency table analytical statistics: Three diseases, allele | |
|---|---|
| Number of missing values | 107 |
| Degree of freedom | 2 |
| Chi-square value | 7.174 |
| Chi-square p value | .0277 |
| G-square value | 7.164 |
| G-square p value | .0278 |
| Contingency table analytical coefficient | .134 |
| Cramer's V value | .136 |

| | Bm. | BM | b.m. | Total |
|---|---|---|---|---|
| Frequency of observation: DPB, allele | | | | |
| Normal | 27 | 60 | 125 | 212 |
| DPB | 15 | 13 | 30 | 58 |
| Total | 42 | 73 | 155 | 270 |
| Percent (row): DPB, alle | | | | |
| Normal | 13 | 28 | 59 | 100 |
| DPB | 26 | 22 | 52 | 100 |
| Total | 16 | 27 | 57 | 100 |

| Contingency table analytical statistics: DPB, allele | |
|---|---|
| Number of missing values | 227 |
| Degree of freedom | 2 |
| Chi-square value | 6.044 |
| Chi-square p value | .0487 |
| G-square value | 5.488 |
| G-square p value | .0643 |
| Contingency table analytical coefficient | .148 |
| Cramer's V value | .150 |

| | Bm. | BM | b.m. | Total |
|---|---|---|---|---|
| Frequency of observation: BE, allele | | | | |
| BE | 16 | 21 | 39 | 76 |
| Normal | 27 | 60 | 125 | 212 |
| Total | 43 | 81 | 164 | 288 |
| Percent (row): BE, allele | | | | |
| BE | 21 | 28 | 51 | 100 |
| Normal | 13 | 28 | 59 | 100 |
| Total | 15 | 28 | 57 | 100 |

| Contingency table analytical statistics: BE, allele | |
|---|---|
| Number of missing values | 209 |
| Degree of freedom | 2 |
| Chi-square value | 3.175 |
| Chi-square p value | .2044 |
| G-square value | 3.007 |
| G-square p value | .2224 |
| Contingency table analytical coefficient | .104 |
| Cramer's V value | .105 |

| | Bm. | BM | b.m. | Total |
|---|---|---|---|---|
| Frequency of observation: PE, allele | | | | |
| PE | 10 | 12 | 22 | 44 |
| Normal | 27 | 60 | 125 | 212 |
| Total | 37 | 72 | 147 | 256 |
| Percent (row): PE, allele | | | | |
| PE | 23 | 27 | 50 | 100 |
| Normal | 13 | 28 | 59 | 100 |
| Total | 14 | 28 | 57 | 100 |

| Contingency table analytical statistics: PE, allele | |
|---|---|
| Number of missing values | 241 |
| Degree of freedom | 2 |
| Chi-square value | 3.040 |
| Chi-square p value | .2187 |
| G-square value | 2.765 |
| G-square p value | .2510 |
| Contingency table analytical coefficient | .108 |
| Cramer's V value | .109 |

| | Bm. | BM | b.m. | Total |
|---|---|---|---|---|
| Frequency of observation: BA, allele | | | | |
| BA | 2 | 14 | 48 | 64 |
| Normal | 27 | 60 | 125 | 212 |
| Total | 29 | 74 | 173 | 276 |
| Percent (row): BA, allele | | | | |
| BA | 3 | 22 | 75 | 100 |
| Normal | 13 | 28 | 59 | 100 |
| Total | 11 | 27 | 63 | 100 |

| Contingency table analytic statistics: BA, allele | |
|---|---|
| Number of missing values | 221 |
| Degree of freedom | 2 |
| Chi-square value | 7.096 |
| Chi-square p value | .0288 |
| G-square value | 8.264 |
| G-square p value | .0160 |
| Contingency table analytical coefficient | .158 |
| Cramer's V value | .160 |

Allelic Classification (2)

Since the association of the Bm alleles with diseases is considered as strong from the above description, the relation of the number of Bm type alleles with the number of alleles other than the Bm type was analyzed by paying special attention to the type.

In view of the respiratory three disease groups (DPB, BE and PE) belonging to the COPD, the frequency of occurrence of the Bm allele is definitely higher in the patient groups suffering from the respiratory three diseases than that in the normal humans when the patient groups suffering from the three respiratory disease groups are compared with normal humans, and a statistical significant difference was recognized in the deviation of the distribution (p=0.0002). The association of the Bm type alleles with the onset of the respiratory three disease groups (DPB, BE and PE) belonging to the COPD was shown by the comparison described above.

Any of the respiratory three disease groups (DPB, BE and PE) belonging to the COPD had a higher frequency of occurrence than that in normal humans in view of each disease (BE; p=0.012, DPB; p=0.0025 and PE; p=0.0052).

On the other hand, the frequency of occurrence of the Bm type was significantly lower than that in normal humans (p=0.049).

| Frequency of observation: Three diseases, Bm/NotBm | | | |
|---|---|---|---|
| | Bm | NotBm | Total |
| Normal | 27 | 185 | 212 |
| Respiratory 3 diseases | 49 | 129 | 178 |
| Total | 76 | 314 | 390 |

| Percent (row): Three diseases, Bm/NotBm | | | |
|---|---|---|---|
| | Bm | NotBm | Total |
| Normal | 13 | 87 | 100 |
| Respiratory 3 diseases | 28 | 72 | 100 |
| Total | 19 | 81 | 100 |

| Contingency table analytical statistics: Three diseases, Bm/NotBm | |
|---|---|
| Number of missing values | 107 |
| Degree of freedom | 1 |
| Chi-square value | 13.494 |
| Chi-square p value | .0002 |
| G-square value | 13.534 |
| G-square p value | .0002 |
| Contingency table analytical coefficient | .183 |
| Phi | .186 |
| Chi-square value (Yates' continuity correction) | 12.568 |
| Chi-square p value (Yates' continuity correction) | .0004 |
| Fisher's direct method p value | .0003 |

| | Bm | NotBm | Total |
|---|---|---|---|
| Frequency of observation: DPB, Bm/NotBm | | | |
| Normal | 27 | 185 | 212 |
| DPB | 17 | 41 | 58 |
| Total | 44 | 226 | 270 |
| Percent (row): DPB, Bm/NotBm | | | |
| Normal | 13 | 87 | 100 |
| DPB | 29 | 71 | 100 |
| Total | 16 | 84 | 100 |

| Contingency table analytical statistics: DPB, Bm/NotBm | |
|---|---|
| Number of missing values | 227 |
| Degree of freedom | 1 |
| Chi-square value | 9.172 |
| Chi-square p value | .0025 |
| G-square value | 8.202 |
| G-square p value | .0042 |
| Contingency table analytical coefficient | .181 |
| Phi | .184 |
| Chi-square value (Yates' continuity correction) | 7.997 |
| Chi-square p value (Yates' continuity correction) | .0047 |
| Fisher's direct method p value | .0045 |

| Frequency of observation: BE, Bm/NotBm | | | |
|---|---|---|---|
| | Bm | NotBm | Total |
| BE | 19 | 57 | 76 |
| Normal | 27 | 185 | 212 |
| Total | 46 | 242 | 288 |

Percent (row): BE, Bm/NotBm

|  | Bm | NotBm | Total |
|---|---|---|---|
| BE | 25 | 75 | 100 |
| Normal | 13 | 87 | 100 |
| Total | 16 | 84 | 100 |

Contingency table analytical statistics: BE, Bm/NotBm

| | |
|---|---|
| Number of missing values | 209 |
| Degree of freedom | 1 |
| Chi-square value | 6.270 |
| Chi-square p value | .0123 |
| G-square value | 5.824 |
| G-square p value | .0158 |
| Contingency table analytical coefficient | .146 |
| Phi | .148 |
| Chi-square value (Yates' continuity correction) | 5.389 |
| Chi-square p value (Yates' continuity correction) | .0203 |
| Fisher's direct method p value | .0172 |

Frequency of observation: PE, Bm/NotBm

|  | Bm | NotBm | Total |
|---|---|---|---|
| PE | 13 | 31 | 44 |
| Normal | 27 | 185 | 212 |
| Total | 40 | 216 | 256 |

Percent (row): PE, Bm/NotBm

|  | Bm | NotBm | Total |
|---|---|---|---|
| PE | 30 | 70 | 100 |
| Normal | 13 | 87 | 100 |
| Total | 16 | 84 | 100 |

Contingency table analytical statistics: PE, Bm/NotBm

| | |
|---|---|
| Number of missing values | 241 |
| Degree of freedom | 1 |
| Chi-square value | 7.810 |
| Chi-square p value | .0052 |
| G-square value | 6.802 |
| G-square p value | .0091 |
| Contingency table analytical coefficient | .172 |
| Phi | .175 |
| Chi-square value (Yates' continuity correction) | 6.587 |
| Chi-square p value (Yates' continuity correction) | .0103 |

-continued

Contingency table analytical statistics: PE, Bm/NotBm

| | |
|---|---|
| Fisher's direct method p value | .0104 |

Frequency of observation: BA, Bm/NotBm

|  | Bm | NotBm | Total |
|---|---|---|---|
| BA | 2 | 62 | 64 |
| Normal | 27 | 185 | 212 |
| Total | 29 | 247 | 276 |

Percent (row): BA, Bm/NotBm

|  | Bm | NotBm | Total |
|---|---|---|---|
| BA | 3 | 97 | 100 |
| Normal | 13 | 87 | 100 |
| Total | 11 | 89 | 100 |

Contingency table analytic statistics: BA, Bm/NotBm

| | |
|---|---|
| Number of missing values | 221 |
| Degree of freedom | 1 |
| Chi-square value | 4.829 |
| Chi-square p value | .0280 |
| G-square value | 6.035 |
| G-square p value | .0140 |
| Contingency table analytical coefficient | .131 |
| Phi | .132 |
| Chi-square value (Yates' continuity correction) | 3.861 |
| Chi-square p value (Yates' continuity correction) | .0494 |
| Fisher's direct method p value | .0340 |

Individual Classification (1)

Since the association of the Bm type among the three haplotypes with the respiratory diseases is considered as especially deep from the analytical results of the allelic classification, the classification and analysis were made of individuals without the Bm type, individuals having one Bm type (hetero) and individuals having two Bm types (homo) by particularly noticing the Bm type.

As for the respiratory three disease groups (DPB, BE and PE) belonging to the COPD, a significant difference was observed in distribution in relation to the frequency of occurrence of the haplotypic classifications Bm-0.1 and 2 based on the Bm in comparison of the normal humans with the patient groups suffering from the respiratory three diseases (p=0.0093).

A significant difference was observed in the deviation of the distribution of patients developing the DPB and PE with regard to each disease (DPB: p=0.0024 and PE: p=0.0069). There was the tendency even in the BE (p=0.089).

Frequency of observation: Three diseases, Bm.

|  | Bm-0 | Bm-1 | Bm-2 | Total |
|---|---|---|---|---|
| Normal | 79 | 27 | 0 | 106 |
| Respiratory 3 diseases | 54 | 29 | 6 | 89 |
| Total | 133 | 56 | 6 | 195 |

Percent (row): Three diseases, Bm.

|  | Bm-0 | Bm-1 | Bm-2 | Total |
|---|---|---|---|---|
| Normal | 75 | 25 | 0 | 100 |
| Respiratory 3 diseases | 61 | 33 | 7 | 100 |
| Total | 68 | 29 | 3 | 100 |

Contingency table analytical statistics Three diseases, Bm.

| | |
|---|---|
| Number of missing values | 63 |
| Degree of freedom | 2 |
| Chi-square value | 9.360 |
| Chi-square p value | .0093 |
| G-square value | . |
| G-square p value | . |
| Contingency table analytical coefficient | .214 |
| Cramer's V value | .219 |

Frequency of observation: DPB, Bm.

|  | Bm-0 | Bm-1 | Bm-2 | Total |
|---|---|---|---|---|
| Normal | 79 | 27 | 0 | 106 |
| DPB | 17 | 9 | 3 | 29 |
| Total | 96 | 36 | 3 | 135 |

Percent (row): DPB, Bm.

|  | Bm-0 | Bm-1 | Bm-2 | Total |
|---|---|---|---|---|
| Normal | 75 | 25 | 0 | 100 |
| DPB | 59 | 31 | 10 | 100 |
| Total | 71 | 27 | 2 | 100 |

Contingency table analytical statistics: DPB, Bm.

| | |
|---|---|
| Number of missing values | 123 |
| Degree of freedom | 2 |
| Chi-square value | 12.040 |
| Chi-square p value | .0024 |
| G-square value | . |
| G-square p value | . |
| Contingency table analytical coefficient | .286 |
| Cramer's V value | .299 |

|  | Bm-0 | Bm-1 | Bm-2 | Total |
|---|---|---|---|---|
| *Frequency of observation: BE, Bm.* | | | | |
| BE | 23 | 14 | 1 | 38 |
| Normal | 79 | 27 | 0 | 106 |
| Total | 102 | 41 | 1 | 144 |
| *Percent (row): BE, Bm.* | | | | |
| BE | 61 | 37 | 3 | 100 |
| Normal | 75 | 25 | 0 | 100 |
| Total | 71 | 28 | 1 | 100 |

Contingency table analytical statistics: BE, Bm.

| | |
|---|---|
| Number of missing values | 114 |
| Degree of freedom | 2 |
| Chi-square value | 4.834 |
| Chi-square p value | .0892 |
| G-square value | . |
| G-square p value | . |
| Contingency table analytical coefficient | .180 |
| Cramer's V value | .183 |

|  | Bm-0 | Bm-1 | Bm-2 | Total |
|---|---|---|---|---|
| *Frequency of observation: PE, Bm.* | | | | |
| PE | 14 | 6 | 2 | 22 |
| Normal | 79 | 27 | 0 | 106 |
| Total | 93 | 33 | 2 | 128 |
| *Percent (row): PE, Bm.* | | | | |
| PE | 64 | 27 | 9 | 100 |
| Normal | 75 | 25 | 0 | 100 |
| Total | 73 | 26 | 2 | 100 |

Contingency table analytical statistics: PE, Bm.

| | |
|---|---|
| Number of missing values | 130 |
| Degree of freedom | 2 |
| Chi-square value | 9.957 |
| Chi-square p value | .0069 |
| G-square value | . |

-continued

| Contingency table analytical statistics: PE, Bm. | |
|---|---|
| G-square p value | . |
| Contingency table analytical coefficient | .0269 |
| Cramer's V value | .0279 |

Individual Classification (2)

Analysis was made whether or not the Bm haplotype was possessed (Bm-0 vs. Bm-1.2).

As for the respiratory three disease groups (DPB, BE and PE) belonging to the COPD, the frequency of occurrence of individuals having the Bm in the respiratory three disease groups is higher than that in normal humans in comparison thereof with the normal humans, and a significant difference was observed in the deviation of distribution (p=0.039). On the other hand, there were more individuals without the Bm haplotype in BA vice versa, and a significant deviation was noted in the distribution as compared with that in the normal human group (p=0.037).

| Three diseases, Bm-0/Bm-1.2 | | | |
|---|---|---|---|
| | Bm-0 | Bm-1.2 | Total |
| Normal | 79 | 27 | 106 |
| Respiratory 3 diseases | 54 | 35 | 89 |
| Total | 133 | 62 | 195 |

| Percent (row): Three diseases, Bm-0/Bm-1.2 | | | |
|---|---|---|---|
| | Bm-0 | Bm-1.2 | Total |
| Normal | 75 | 25 | 100 |
| Respiratory 3 diseases | 61 | 39 | 100 |
| Total | 68 | 32 | 100 |

| Contingency table analytical statistics: Three diseases, Bm-0/Bm-1.2 | |
|---|---|
| Number of missing values | 63 |
| Degree of freedom | 1 |
| Chi-square value | 4.282 |
| Chi-square p value | .0385 |
| G-square value | 4.279 |
| G-square p value | .0386 |
| Contingency table analytical coefficient | .147 |
| Phi | .148 |
| Chi-square value (Yates' continuity correction) | 3.670 |
| Chi-square p value (Yates' continuity correction) | .0554 |
| Fisher's direct method p value | .0453 |

| Frequency of observation: BA, Bm-0/Bm-1.2 | | | |
|---|---|---|---|
| | Bm-0 | Bm-1.2 | Total |
| BA | 30 | 2 | 32 |
| Normal | 79 | 27 | 106 |
| Total | 109 | 29 | 138 |

| Percent (row): BA, Bm-0/Bm-1.2 | | | |
|---|---|---|---|
| | Bm-0 | Bm-1.2 | Total |
| BA | 94 | 6 | 100 |
| Normal | 75 | 25 | 100 |
| Total | 79 | 21 | 100 |

| Contingency table analytical statistics: BA, Bm-0/Bm-1.2 | |
|---|---|
| Number of missing values | 120 |
| Degree of freedom | 1 |
| Chi-square value | 5.471 |
| Chi-square p value | .0193 |
| G-square value | 6.641 |
| G-square p value | .0100 |
| Contingency table analytical coefficient | .195 |
| Phi | .199 |
| Chi-square value (Yates' continuity correction) | 4.375 |
| Chi-square p value (Yates' continuity correction) | .0365 |
| Fisher's direct method p value | .0241 |

| Frequency of observation: DPB, Bm-0/Bm-1.2 | | | |
|---|---|---|---|
| | Bm-0 | Bm-1.2 | Total |
| Normal | 79 | 27 | 106 |
| DPB | 17 | 12 | 29 |
| Total | 96 | 39 | 135 |

| Percent (row): DPB, Bm-0/Bm-1.2 | | | |
|---|---|---|---|
| | Bm-0 | Bm-1.2 | Total |
| Normal | 75 | 25 | 100 |
| DPB | 59 | 41 | 100 |
| Total | 71 | 29 | 100 |

| Contingency table analytical statistics: DPB, Bm-0/Bm-1.2 | |
|---|---|
| Number of missing values | 123 |
| Degree of freedom | 1 |
| Chi-square value | 2.805 |
| Chi-square p value | .0940 |
| G-square value | 2.674 |
| G-square p value | .1020 |
| Contingency table analytical coefficient | .143 |
| Phi | .144 |
| Chi-square value (Yates' continuity correction) | 2.089 |
| Chi-square p value (Yates' continuity correction) | .1484 |
| Fisher's direct method p value | .1086 |

| Frequency of observation: BE, Bm-0/Bm-1.2 | | | |
|---|---|---|---|
| | Bm-0 | Bm-1.2 | Total |
| BE | 23 | 15 | 38 |
| Normal | 79 | 27 | 106 |
| Total | 102 | 42 | 144 |

| Percent (row): BE, Bm-0/Bm-1.2 | | | |
|---|---|---|---|
| | Bm-0 | Bm-1.2 | Total |
| BE | 61 | 39 | 100 |
| Normal | 75 | 25 | 100 |
| Total | 71 | 29 | 100 |

| Contingency table analytical statistics: BE, Bm-0/Bm-1.2 | |
|---|---|
| Number of missing values | 114 |
| Degree of freedom | 1 |
| Chi-square value | 2.654 |
| Chi-square p value | .1033 |
| G-square value | 2.564 |
| G-square p value | .1093 |
| Contingency table analytical coefficient | .135 |
| Phi | .136 |
| Chi-square value (Yates' continuity correction) | 2.020 |
| Chi-square p value (Yates' continuity correction) | .1552 |
| Fisher's direct method p value | .1444 |

| Frequency of observation PE, Bm-0/Bm-1.2 | | | |
|---|---|---|---|
| | Bm-0 | Bm-1.2 | Total |
| PE | 14 | 8 | 22 |
| Normal | 79 | 27 | 106 |
| Total | 93 | 35 | 128 |

| Percent (row): PE, Bm-0/Bm-1.2 | | | |
|---|---|---|---|
| | Bm-0 | Bm-1.2 | Total |
| PE | 64 | 36 | 100 |
| Normal | 75 | 25 | 100 |
| Total | 73 | 27 | 100 |

| Contingency table analytical statistics PE, Bm-0/Bm-1.2 | |
|---|---|
| Number of missing values | 130 |
| Degree of freedom | 1 |
| Chi-square value | 1.088 |
| Chi-square p value | .2969 |
| G-square value | 1.040 |
| G-square p value | .3079 |
| Contingency table analytical coefficient | .092 |
| Phi | .092 |
| Chi-square value (Yates' continuity correction) | .609 |
| Chi-square p value (Yates' continuity correction) | 4.353 |
| Fisher's direct method p value | .3035 |

Individual Classification (3)

Furthermore, a comparison of the frequency of occurrence (Bm-0.1 vs. Bm-2) was made between individuals having the Bm haplotype as the homo (BBmm; Bm-2) and individuals without the haplotype (Bm-0.1). As for the respiratory three disease groups (DPB, BE and PE) belonging to the COPD, a significant difference was observed in the frequency of occurrence between the individuals having the Bm haplotype as the homo (BBmm) and individuals without the Bm haplotype in comparison of the respiratory three disease groups with the normal humans (p=0.021), and all the six individuals having the Bm homo type (Bm-2) were affected by any of the respiratory three diseases (DPE, BE and PE) belonging to the COPD. Three individuals were affected by the DPB and one thereof was affected by the BE. No human having the Bm homo type (Bm-2) was found in 106 normal humans and 32 patients suffering from the BA.

As for each disease, a statistical significant difference was observed in the deviation of the distribution of patients suffering from the DPB and PE (DPB: p=0.0082 and PE: p=0.029).

Frequency of observation: Three diseases, Bm-0.1/Bm-2

|  | Bm-0.1 | Bm-2 | Total |
|---|---|---|---|
| Normal | 106 | 0 | 106 |
| Respiratory 3 diseases | 83 | 6 | 89 |
| Total | 189 | 6 | 195 |

Percent (row): Three diseases, Bm-0.1/Bm-2.

|  | Bm-0.1 | Bm-2 | Total |
|---|---|---|---|
| Normal | 100 | 0 | 100 |
| Respiratory 3 diseases | 93 | 7 | 100 |
| Total | 97 | 3 | 100 |

Contingency table analytical statistics: Three diseases, Bm-0.1/Bm-2

| | |
|---|---|
| Number of missing values | 63 |
| Degree of freedom | 1 |
| Chi-square value | 7.373 |
| Chi-square p value | .0066 |
| G-square value | . |
| G-square p value | . |
| Contingency table analytical coefficient | .191 |
| Phi | .194 |
| Chi-square value (Yates' continuity correction) | 5.295 |
| Chi-square p value (Yates' continuity correction) | .0214 |
| Fisher's direct method p value | .0082 |

Frequency of observation: DPB, Bm-0.1/Bm-2

|  | Bm-0.1 | Bm-2 | Total |
|---|---|---|---|
| Normal | 106 | 0 | 106 |
| DPB | 26 | 3 | 29 |
| Total | 132 | 3 | 135 |

Percent (row): DPB, Bm-0.1/Bm-2

|  | Bm-0.1 | Bm-2 | Total |
|---|---|---|---|
| Normal | 100 | 0 | 100 |
| DPB | 90 | 10 | 100 |
| Total | 98 | 2 | 100 |

Contingency table analytical statistics: DPB, Bm-0.1/Bm-2

| | |
|---|---|
| Number of missing values | 123 |
| Degree of freedom | 1 |
| Chi-square value | 11.215 |
| Chi-square p value | .0008 |
| G-square value | . |
| G-square p value | . |
| Contingency table analytical coefficient | .277 |
| Phi | .288 |
| Chi-square value (Yates' continuity correction) | 6.987 |
| Chi-square p value (Yates' continuity correction) | .0082 |
| Fisher's direct method p value | .0091 |

Frequency of observation: PE, Bm-0.1/Bm-2

|  | Bm-0.1 | Bm-2 | Total |
|---|---|---|---|
| PE | 20 | 2 | 22 |
| Normal | 106 | 0 | 106 |
| Total | 126 | 2 | 128 |

Percent (row): PE, Bm-0.1/Bm-2

|  | Bm-0.1 | Bm-2 | Total |
|---|---|---|---|
| PE | 91 | 9 | 100 |
| Normal | 100 | 0 | 100 |
| Total | 98 | 2 | 100 |

Contingency table analytical statistics: PE, Bm-0.1/Bm-2

| | |
|---|---|
| Number of missing values | 130 |
| Degree of freedom | 1 |
| Chi-square value | 9.789 |
| Chi-square p value | .0018 |
| G-square value | . |
| G-square p value | . |
| Contingency table analytical coefficient | .267 |
| Phi | .277 |
| Chi-square value (Yates' continuity correction) | 4.771 |
| Chi-square p value (Yates' continuity correction) | 0289 |
| Fisher's direct method p value | .0284 |

| Frequency of observation: BE, Bm-0.1/Bm-2 | | | |
|---|---|---|---|
| | Bm-0.1 | Bm-2 | Total |
| BE | 37 | 1 | 38 |
| Normal | 106 | 0 | 106 |
| Total | 143 | 1 | 144 |

| Percent (row): BE, Bm-0.1/Bm-2 | | | |
|---|---|---|---|
| | Bm-0.1 | Bm-2 | Total |
| BE | 97 | 3 | 100 |
| Normal | 100 | 0 | 100 |
| Total | 99 | 1 | 100 |

| Contingency table analytical statistics: BE, Bm-0.1/Bm-2 | |
|---|---|
| Number of missing values | 114 |
| Degree of freedom | 1 |
| Chi-square value | 2.809 |
| Chi-square p value | .0937 |
| G-square value | . |
| G-square p value | . |
| Contingency table analytical coefficient | .138 |
| Phi | .140 |
| Chi-square value (Yates' continuity correction) | .289 |
| Chi-square p value (Yates' continuity correction) | .5909 |
| Fisher's direct method p value | .2639 |

| Frequency of observation: BA, Bm-0.1/Bm-2 | | | |
|---|---|---|---|
| | Bm-0.1 | Bm-2 | Total |
| BA | 32 | 0 | 32 |
| Normal | 106 | 0 | 106 |
| Total | 138 | 0 | 138 |

| Percent (row): BA, Bm-0.1/Bm-2 | | | |
|---|---|---|---|
| | Bm-0.1 | Bm-2 | Total |
| BA | 100 | 0 | 100 |
| Normal | 100 | 0 | 100 |
| Total | 100 | 0 | 100 |

The above results definitely show that the Bm type haplotypes are associated with chronic respiratory tract inflammations in respiratory diseases according to a certain mechanism by analyzing the intron genetic polymorphisms of the human trypsin-like enzyme of the respiratory tract. Furthermore, it is also shown that the association of the human trypsin-like enzyme of the respiratory tract with diseases is different between the three diseases of DPB, BE and PE belonging to the chronic obstructive pulmonary diseases (COPD) and the BA.

Since all the individuals having a certain genetic polymorphism do not develop some diseases, the genetic polymorphisms of the human trypsin-like enzyme of the respiratory tract are not a decisive onset factor such as the so-called genetic disease and may safely be said as a readily onsetting factor. That is, when an environmental factor or the like is added to individuals having the Bm haplotypes, the individuals are susceptible to the onset of the respiratory diseases such as the BE, PE and DPB.

It is shown from the above results that diseases associated with the human trypsin-like enzyme of the respiratory tract can be classified by using the genetic polymorphisms of the human trypsin-like enzyme of the respiratory tract. The analytical method for the genetic polymorphisms of the human trypsin-like enzyme of the respiratory tract is a means applicable to the prediction of onset constitution of diseases associated with the human trypsin-like enzyme of the respiratory tract in individual humans, the prediction of effects on the treatment of the diseases, prediction of the possibility for relapse of the prognosis thereof or the like.

POSSIBILITY OF INDUSTRIAL UTILIZATION

The present invention provides a method for determining the disease-associated constitution of individual humans by the analyzing the genetic polymorphisms of the human trypsin-like enzyme of the respiratory tract. Accordingly, when the diseases associated with the human trypsin-like enzyme of the respiratory tract can be identified by the analysis, it can be assumed that individuals having the certain genotype of the human trypsin-like enzyme of the respiratory tract are susceptible to some diseases.

That is, information about the methods of treatment for the individual humans can be provided in an early stage by predicting the disease onset constitution (individuals having the constitution susceptible to certain diseases) and related with early diagnosis and early treatment. The possibility for the relapse of the diseases can be estimated even after the treatment. That is, physicians can pay careful attention to patients and provide proper direction by predicting the prognosis of the treatment (the course of curing after the treatment of patients and risk of relapse)

Furthermore, the genetic polymorphic analysis of the human trypsin-like enzyme of the respiratory tract has a possibility for providing a means for determining effects of drugs to be administered and narrowing the patient groups in which the administered drugs are effective in the development of the drugs in the morbid state associated with the human trypsin-like enzyme of the respiratory tract.

As described above, the early diagnosis, early treatment and direction of proper prophylactic methods, appropriate medication and proper after follow after the treatment are related to a reduction in huge medical expenditures causing problems at present.

SEQUENCE LISTING

<160> NUMBER OF SEQ ID NOS: 17

<210> SEQ ID NO 1
<211> LENGTH: 107
<212> TYPE: DNA
<213> ORGANISM: Homo sapiens

<400> SEQUENCE: 1
gtgaggccac cactacctac ccatctggga acaattagaa tagacaggtc atgaagactg    60
caccctctac cctaggattg aattgagcca gaaataattc aatgcaa                 107

<210> SEQ ID NO 2
<211> LENGTH: 150
<212> TYPE: DNA
<213> ORGANISM: Homo sapiens

<400> SEQUENCE: 2
taaactcact tgccagctat aatgcaggaa atatagcaag agatgtggat ccaatagttc    60
tagatagtgg tacaggatgg ctaagatgaa ttatatatct gaaatgttca caaattccct   120
actcatatag catgtttcat aatgttttag                                    150

<210> SEQ ID NO 3
<211> LENGTH: 163
<212> TYPE: DNA
<213> ORGANISM: Homo sapiens

<400> SEQUENCE: 3
gtaagtgtct cggaaaaaaa aattaacaat agaaatgtct tatatttgct attaggtaat    60
tttttaaatt aggaaacatc tggaataggt gtttctattc ttctacagac agaaccattc   120
tatattctgc tcagcccaag ctctggctac ccctgagtct cct                     163

<210> SEQ ID NO 4
<211> LENGTH: 177
<212> TYPE: DNA
<213> ORGANISM: Homo sapiens

<400> SEQUENCE: 4
tcctcatcta cttggggaat tttggctgcg aagaaactcc aaagtaaatc tttagaagcc    60
ttcattgtta aatatgaaat aatgtttgga gtacatttat ttcttctcaa atttattata   120
gggtcaataa tgtacacatc ttgaagtcca ttttttttcct gcttttataa caaacag     177

<210> SEQ ID NO 5
<211> LENGTH: 120
<212> TYPE: DNA
<213> ORGANISM: Homo sapiens

<400> SEQUENCE: 5
gtaagctcaa gacaatctca tccatgtcat catccaagaa gtgtataagc acttcctagt    60
atgtgataat gtgatagaca taagtgtaac agttacaata cacagccctg ttcctctaaa   120

<210> SEQ ID NO 6
<211> LENGTH: 125
<212> TYPE: DNA
<213> ORGANISM: Homo sapiens

<400> SEQUENCE: 6
ggaaataggc tgactttatt tgtataatga atgtgactcc ttcctcgact gccatagaaa    60

```
taaactcctt aatattttgg gtttgtcttt gcacttaagt aatcagtcat tctgtttttt      120
tacag                                                                 125

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: primer A1

<400> SEQUENCE: 7
aagtcagtct gcggctcaat aatgcccacc actgt                                 35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: primer A2

<400> SEQUENCE: 8
ctcattctta gtttaggaaa tgttgtggaa atacc                                 35

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: primer B1

<400> SEQUENCE: 9
acccagaata ttccacctgg ctctactgct tatgt                                 35

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: primer B2

<400> SEQUENCE: 10
cattacttat tattctgacc tgtccttgcc ttagc                                 35

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: primer C1

<400> SEQUENCE: 11
ggagccatct tgtctggaat gctgtgtgct ggagt                                 35

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: primer C2

<400> SEQUENCE: 12
cacaataaac caaagccgcc gtgagtcttc ttgta                                 35

<210> SEQ ID NO 13
```

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: primer D1

<400> SEQUENCE: 13
tgtcgtcgca ggggtagtga tcctggcagt cacca                              35

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: primer D2

<400> SEQUENCE: 14
ttcaattctt ccactcaaag tcctgtattc ctgtg                              35

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: primer E1

<400> SEQUENCE: 15
tgaggcaaga tggtagtggt gtgagagcgg atgtt                              35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: primer E2

<400> SEQUENCE: 16
ggccagcttc cctcctcagc ctcagtgcct ccaag                              35

<210> SEQ ID NO 17
<211> LENGTH: 3376
<212> TYPE: DNA
<213> ORGANISM: Homo sapiens

<400> SEQUENCE: 17
gaattcggct tggagccatc ttgtctggaa tgctgtgtgc tggagtacct caaggtggag      60
tggacgcatg tcaggtaagc tcaagacaat ctcatccatg tcatcatcca agaagtgtat     120
aagcacttcc tagtatgtga taatgtgata gacataagtg taacagttac aatacacagc     180
cctgttcctc taaaatttat aatctagatt ttagaaataa attttttat gaatgaagtt      240 tatctatcat gaaagcatta actctgagag gccaaattac agagtagtta accatccaaa     300
gctcaagaat cagaaagacc tcgatttgaa ttccttaacc tctattacca agtctcttta     360
actaaaagct ggggataatc ataatagcac ctaactttt gggtactaag aaaagttaaa      420
tgaagactaa atatatcagg cacatggtaa acaacaaaga aatctcatct atttcactat     480
tattaatgta gaccatggtc actcgtgtta ataactttaa cctcaacctt ttaactgcta     540
tgaaggatta aataaaaaat taatcactat attataaaaa ttaattgata tataataaat     600
gaatttaaga aatacgtaat aattcatgga ctccttgaag atagaaaatt tatacaaaat     660
cctagtaatt tgagtcacaa aagctcctac aataatgaaa cagtatgaat gaaaaagaaa     720
agaaataact attatatttg gatctagccc ataatttta accaaatgca caaaacaaa      780

```
caacaaatat gaaattctca ctgtaaagtg attaaaatca aatttgaatt ctaaaatttt      840
aaattaaatt atctaaacat aattgatgca gttatatgtt ttaataggtt ttgttcacat      900
atctgaaatc caactccaca tagtagcagg aacagctggt gtcagaaatt aaatattctt      960
ttagtctgga gttttaaaaa atcaatctgt ttacttgagt aatttgttgc tgttttcatg     1020
ggtgaattgt atacagaagg ataggaatta ttcttcgcat caaaaggtca ctgactttca     1080
tatttagtgc tcatggtctt taaaaaatgg ataaaaagta gttctcacat ttcatggaaa     1140
gcccccaatc catgagcaca tttcccaaaa ttgaaacatt tttatcaact gcaagttgtg     1200
tgtaggtgga gatttgtttt tcaattgtca agatactgtt aattacccag tcctttatct     1260
ccttttggtg gagatgtctc tgtgctagga aaccttctt gctctccttc ctgtttctct      1320
tttactactg gccctgaaac aacaaattct caagtttcat gacagctttc caagaatcc      1380 atcaatcaaa taagcaacac aactcgacac tgacaattcc agacctacta agagcattaa     1440
ttaagactta aaaataaaca tgagttttaa aagggtgtta ttcattattt tcccatttat     1500
aacgtccctt accttctgtc cttcagtgca tacaaattat tatcttcctt gaagcccagt     1560
tcaagccgta cctcaccatg ataccttcca tgtatattcc actccaggcc tcactgattt     1620
ttaactgaaa tactataatg catagttcac aattaaaaaa aaaaaaaaca cagcacttta     1680
cataagagct tacaggatcc tatttgtttt atccattctt ttgttcattt ttacaatcat     1740
taattcaaag gaattatatt aattactttc tatgcacccg acgttgtgtt aacacaacaa     1800
tactatccct gcattcagca agtctatggt ctacaagaga ggacacaaat tcaaatgtct     1860
gtagtcaagc agtgaagctg gctagatatg gaaaaattac aagtccctct tgctttaaca     1920
tttgcttgcc cacatttgat cagacatcat gcaaataat ttctcactat agagaaaaaa      1980
acactacaaa accaataata taagaactg agaactggtt tactgaagca tgcatatgtc      2040
atctaaaaga agcaggtgac gaccagcttc atgaagtact tgccatgcat attggcactt     2100
cacacactga cccttctccc cacctagacc agtaattaaa caggtatgga tgagctagct     2160
actaagagca gccaactgaa tagctgacta atttagaagc acacttggta ataatagctg     2220
acttttatta gtactgacta tactatatgc taagctgtac tcaaagtgct ttgagtttta     2280
aactgataca aacattatat gaggaaacag aggtacagag agctattcac cagcttacca     2340
aaggtcacat agctggtaag tggaggactt aaacccagac tatctagttt cagaacgcgc     2400
agacttaatc catcgtgcag aacataagac atactccatc tgtctcccca actaggttat     2460
tatgtgcaca aatatttatt ggttggttgg ttcattatta tgactgggtg gtaagtatgt     2520
cattaggagt gttttgctta tgactatata aatttcttca ccaaaagaag actttctgat     2580
gatatactat gcatcagaca ccacgcaggg tgctaaggtt aggaagataa gtgagacttc     2640
tagaaactca ttcattcaac aaatatctcc taagggctag aagcttaggt ttcagcagtg     2700
aacagaatag gtatgttctc tttcgtgttg gaccttatag tatatctggg aaaacagaca     2760
ttgaataaat atcacaaatg caagtgagtg tttcagagac atgcagctgc tacatcaaac     2820 caaacagaa caaaacaaac aacccaaaaa ctgaccagtg ggattaagtg taaataggca     2880
cacaaatgca caaatatgct tttataaaat agtgaagcag tgacagagac acacacaaga     2940
tataaagaca caatgaagaa caattgagcc caaagctgga aagggtgaga gtgtgaagga     3000
aaaaggttga tcagagaagt tttcccgaag gagagaaagc ctggatgatt aggaggcaac     3060
cactcggtga ctgagggaaa tctgaaaaat gtatttgtca tcttctcaga cttgctgaag     3120
```

| | | | | | |
|---|---|---|---|---|---|
| gaatgacttg | ggtactttga | ggatttcagt | aatttttcca | tgacttggta | taatatttca 3180 |
| aaaggaaata | ggctgacttt | atttgtataa | tgaatgtgac | tccttcctcg | actgccatag 3240 |
| aaataaactc | cttaatattt | tgggtttgtc | tttgcactta | agtaatcagt | cattctgttt 3300 |
| ttttacaggg | tgactctggt | ggcccactag | tacaagaaga | ctcacggcgg | ctttggttta 3360 |
| ttgtgaagcc | gaattc | | | | 3376 |

What is claimed is:

1. A method for predicting susceptibility to the onset of an obstructive pulmonary disease in a human, comprising:
   (a) amplifying intron C of a human trypsin-like enzyme gene to produce a 3.4 kb amplification product that comprises intron C;
   (b) digesting the amplification product of step (a) with restriction endonuclease BstUI; and
   (c) detecting the presence of a 3.4 kb undigested amplification product as indicative of a BB genotype, wherein the presence of said genotype is indicative of susceptibility to onset of said obstructive pulmonary disease.

2. The method of claim 1 wherein the obstructive pulmonary disease is diffuse panbronchiolitis, bronchiectasis, or pulmonary emphysema.

3. The method of claim 1, wherein a primer pair comprising SEQ ID NO: 11 and SEQ ID NO: 12 is used in amplifying step (a).

4. A method for predicting susceptibility to the onset of an obstructive pulmonary disease in a human, comprising:
   (a) amplifying intron C of a human trypsin-like enzyme gene to produce a 3.4 kb amplification product that comprises intron C;
   (b) digesting the amplification product of step (a) with restriction endonuclease BstUI and separately digesting the amplification product of step (a) with restriction endonuclease MboI; and
   (c) detecting the presence of a 3.4 kb undigested amplification product from the BstUI digestion and a 1.05 kb restriction fragment from the MboI digestion as indicative of a Bm haplotype, wherein the presence of said haplotype is indicative of susceptibility to onset of said obstructive pulmonary disease.

5. The method of claim 4 wherein the obstructive pulmonary disease is diffuse panbronchiolitis, bronchiectasis, or pulmonary emphysema.

6. The method of claim 4, wherein a primer pair comprising SEQ ID NO: 11 and SEQ ID NO: 12 is used in amplifying step (a).

7. A nucleic acid fragment of an intron of a human trypsin-like enzyme gene wherein said nucleic acid fragment is prepared by a method consisting essentially of amplifying an intron of a human trypsin-like enzyme gene with a primer pair comprising SEQ ID NO: 11 and SEQ ID NO: 12.

8. A nucleic acid fragment of an intron of a human trypsin-like enzyme gene comprising SEQ ID NO: 5 or SEQ ID NO: 6.

9. A nucleic acid fragment of an intron of a human trypsin-like enzyme gene comprising SEQ ID NO: 17.

* * * * *